US012605587B2

(12) United States Patent
Roy et al.

(10) Patent No.: US 12,605,587 B2
(45) Date of Patent: Apr. 21, 2026

(54) AUTOMATIC ARM TRAINING DEVICE, SYSTEM, AND METHOD

(71) Applicants:University Of Maryland, Baltimore, Baltimore, MD (US); NEXTSTEP ROBOTICS, INC., Baltimore, MD (US)

(72) Inventors: Anindo Roy, Baltimore, MD (US); Richard F. Macko, Ellicott City, MD (US); Bradley Hennessie, Columbia, MD (US)

(73) Assignees: University of Maryland, Baltimore, MD (US); NEXTSTEP ROBOTICS, INC., Baltimore, MD (US)

( * ) Notice: Subject to any disclaimer, the term of this patent is extended or adjusted under 35 U.S.C. 154(b) by 856 days.

(21) Appl. No.: 17/786,679

(22) PCT Filed: Dec. 17, 2020

(86) PCT No.: PCT/US2020/065605
§ 371 (c)(1),
(2) Date: Jun. 17, 2022

(87) PCT Pub. No.: WO2021/127173
PCT Pub. Date: Jun. 24, 2021

(65) Prior Publication Data
US 2023/0025266 A1     Jan. 26, 2023

Related U.S. Application Data

(60) Provisional application No. 62/949,128, filed on Dec. 17, 2019.

(51) Int. Cl.
*A63B 21/00*     (2006.01)
*A61B 5/00*     (2006.01)
*A63B 21/005*     (2006.01)

(52) U.S. Cl.
CPC ........ *A63B 21/4007* (2015.10); *A61B 5/6895* (2013.01); *A61B 5/744* (2013.01); *A63B 21/0058* (2013.01); *A61B 2505/09* (2013.01)

(58) Field of Classification Search
CPC ............ A63B 21/4007; A63B 21/0058; A61B 5/6895; A61B 5/744; A61B 5/224; A61B 2505/09
(Continued)

(56) References Cited

U.S. PATENT DOCUMENTS 3,984,646 A     10/1976   Day
4,592,531 A     6/1986   Schihl
(Continued)

FOREIGN PATENT DOCUMENTS

WO     2011/076240 A1     6/2011

OTHER PUBLICATIONS

Carey, J. R., et al., "Electromyographic Study of Muscular Overflow During Precision Handgrip", Physical Therapy, vol. 63, Issue 4, 1983, pp. 505-511.
(Continued)

*Primary Examiner* — Peter J Macchiarolo
*Assistant Examiner* — John M Royston
(74) *Attorney, Agent, or Firm* — Wolter Van Dyke Davis, PLLC; Eugene J. Molinelli; Patrick D. Herron

(57)     ABSTRACT

A method and apparatus for automated arm training includes at least one therapeutic device that includes a handle, a sensor assembly, and a display. The handle is configured to move along a path. The sensor assembly is configured to provide a measured time series made up of multiple handle location measurements at a corresponding multiple of measured time instances. The display is configured to present an
(Continued)

image based on the measured time series. A robot motor can be configured to keep the handle moving near a tolerance of a target trajectory.

25 Claims, 25 Drawing Sheets

(58) Field of Classification Search
USPC ...................................................... 73/379.01
See application file for complete search history.

(56) References Cited

U.S. PATENT DOCUMENTS

| 4,660,431 | A | 4/1987 | Heine |
|---|---|---|---|
| 4,689,540 | A | 8/1987 | Tani et al. |
| 4,947,166 | A | 8/1990 | Wingate et al. |
| 5,186,695 | A | 2/1993 | Mangseth et al. |
| H1363 | H | 10/1994 | Leeker |
| 8,162,108 | B2 | 4/2012 | Sirigu et al. |
| 9,943,459 | B2 | 4/2018 | Roy et al. |
| 10,471,297 | B1 * | 11/2019 | Smith ............... A63B 24/0087 |
| 2006/0293617 | A1 | 12/2006 | Einav et al. |
| 2013/0091995 | A1 * | 4/2013 | Brooks .................... B26D 7/18 |
| | | | 83/99 |
| 2013/0196300 | A1 * | 8/2013 | Huang ................... G09B 23/28 |
| | | | 434/262 |

OTHER PUBLICATIONS

Cauraugh, J. H., et al., "Two Coupled Motor Recovery Protocols Are Better Than One", Electromyogram-Triggered Neuromuscular Stimulation and Bilateral Movements, Stroke, vol. 33, No. 6, 2002, 6 pages.
Forrester, L. W., et al., "Task-specific ankle robotics gait training after stroke: a randomized pilot study", Journal of NeuroEngineering and Rehabilitation, vol. 13, No. 51, 2016, 6 pages.
Forrester, L. W., et al., "Ankle Training With a Robotic Device Improves Hemiparetic Gait After a Stroke", Neurorehabil Neural Repair, vol. 25, No. 4, May 2011, 369-377.
Forrester, L. W., et al., "Modular Ankle Robotics Training in Early Subacute Stroke: A Randomized Controlled Pilot Study", Neurorehabil Neural Repair, vol. 28, No. 7, Sep. 2014, pp. 678-687.
Geffen, M. G., et al., "Interhemispheric control of manual motor activity", Beh. Brain Res., vol. 64, Issue 1-2, 1994, pp. 131-140.
Goodman, R. N., et al., "Increased reward in ankle robotics training enhances motor control and cortical efficiency in stroke", JRRD, vol. 51, No. 2, 2014, 16 pages.
Gowland, C., et al., "Agonist and Antagonist Activity During Voluntary Upper-Limb Movement in Patients with Stroke", Physical Therapy, vol. 72, Issue 9, 1992, pp. 624-633.
Green, J. B., "An electromyographic study of mirror movements", Neurology, vol. 17, Issue 1, 1967, pp. 91-94.
Hogan, N., et al., "Impedance Control: An Approach to Manipulation: Part II—Implementation ", J. Dyn. Sys., Meas., Control. Mar, vol. 107, No. 1, 1985, pp. 8-16.
International Preliminary Report on Patentability received for PCT Patent Application No. PCT/US2020/065605, mailed on Jun. 30, 2022, 10 pages.
International Search Report and Written Opinion received for PCT Patent Application No. PCT/US2020/065605, mailed on Mar. 16, 2021, 12 pages.
Jorgensen, H. S., et al., "Outcome and time course of recovery in stroke. Part II: Time course of recovery. The Copenhagen Stroke Study", Archives of Phys. Med. and Rehab., vol. 76, 1995, pp. 406-412.
Jorgensen, MD. H. S., et al., "Outcome and time course of recovery in stroke. Part I: Outcome. The Copenhagen stroke study", Archives of Physical Medicine and Rehabilitation, vol. 76, No. 5, May 1995, pp. 399-405.

Kelso, J. A. S., et al., "Converging evidence in support of common dynamical principles for speech and movement coordination", American Journal of Physiology, vol. 246, 1984, pp. 928-935.
Kelso, J. A. S., et al., "On the coordination of two-handed movements", J. of Experim Psycho-Human Percep and Perf., vol. 5, 1979, pp. 229-238.
Kelso, J. A. S., et al., "On the space-time structure of human interlimb co-ordination", The Quarterly Journal of Experimental Psychology Section A, vol. 35, Issue 2, 1983, pp. 347-375.
Kwakkel, G., et al., "Predicting Disability in Stroke—A Critical Review of the Literature ", Age and Ageing, vol. 25, No. 6, Nov. 1996, pp. 479-489.
Lo, A. C., et al., "Robot-Assisted Therapy for Long-Term Upper-Limb Impairment after Stroke", N. Eng. J. Med., vol. 362, 2011, pp. 1772-1783.
Locke, E. A., et al., "Cognitive aspects of psychomotor performance: The effects of performance goals on level of performance.", Journal of Applied Psychology, vol. 50, No. 4, 1966, pp. 286-291.
Luft, A. R., et al., "Repetitive Bilateral Arm Training and Motor Cortex Activation in Chronic Stroke", J. of American Med Association, vol. 292, No. 15, 2004, pp. 1853-1862.
Mccombe, W. S., et al., "Fine motor control in adults with and without chronic hemiparesis: baseline comparison to nondisabled adults and effects of bilateral arm training", Arch. Phys. Med. Rehabil., vol. 85, No. 7, pp. 1076-1083.
Micheal, P., "Simultaneous performance of two motor activities: The factor of timing", Neuropsychologia, vol. 15, Issue 3, 1977, pp. 461-465.
Mudie, M. H., et al., "Can simultaneous bilateral movement involve the undamaged hemisphere in reconstruction of neural networks damaged by stroke?", Disability and Rehabilitation , vol. 22, No. 1-2, 2000, 15 pages.
Nakayama, H., et al., "Compensation in recovery of upper extremity function after stroke: the Copenhagen Stroke Study", Archives of Physical Med. and Rehab., vol. 75, 1994, pp. 852-857.
Olsen, T. S., et al., "Improvement of Function and Motor Impairment After Stroke", Neurorehabilitation and Neural Repair, vol. 3, 1989, pp. 187-192.
Rohrer, B., et al., "Movement Smoothness Changes during Stroke Recovery", The Journal of Neuroscience, vol. 22, No. 18, Sep. 15, 2022, pp. 8297-8304.
Roy, A., et al., "Anklebot-assisted locomotor training after stroke: A novel deficit-adjusted control approach", IEEE International Conference on Robotics and Automation, May 2013, 8 pages.
Roy, A., et al., "Quantifying Human Autonomy Recovery During Ankle Robot-Assisted Reversal of Foot Drop After Stroke", 2018 IEEE Int Conf Biomed Robotics and Biomechatronics, 2018, pp. 523-530.
Roy, A., et al., "Robot-Aided Neurorehabilitation: A Novel Robot for Ankle Rehabilitation", IEEE Trans. Robotics, vol. 25, Issue 3, 2009, pp. 569-582.
Roy, A., et al., "Short-term ankle motor performance with ankle robotics training in chronic hemiparetic stroke", Journal of Rehabilitation Research & Development, vol. 48, No. 4, 2011, pp. 417-430.
Salmoni, A. W., et al., "Knowledge of results and motor learning: A review and critical reappraisal.", Psychological Bulletin, vol. 95, No. 3, 1984, pp. 355-386.
Schmidt, R. C., et al., "Phase transitions and critical fluctuations in the visual coordination of rhythmic movements between people", Journal of Experimental Psychology, vol. 16, 1990, pp. 227-247.
Stinear, J. W., et al., "Disinhibition in the human motor cortex is enhanced by synchronous upper limb movements", J. Physiol., vol. 543, 2002, pp. 307-316.
Swinnen, S. P., et al., "The coordination of limb movements with different kinematic patterns", Brain and Cognition, vol. 8, Issue 3, 1988, pp. 326-347.
Thaut, M. H., et al., "Effect of Rhythmic Auditory Cuing on Temporal Stride Parameters and EMG. Patterns in Hemiparetic Gait of Stroke Patients", Neurorehabilitation and Neural Repair, vol. 7, 1993, pp. 9-16.

(56)                    References Cited

OTHER PUBLICATIONS

Thaut, M. H., et al., "Kinematic optimization of spatiotemporal patterns in paretic arm training with stroke patients", Neuropsychologia, vol. 40, No. 7, 2002, pp. 1073-1081.
Thaut, M. H., et al., "Rhythmic facilitation of gait training in hemiparetic stroke rehabilitation", Journal of the Neurological Sciences, vol. 151, No. 2, Oct. 22, 1997, pp. 207-212.
Waller, S. M., et al., "Bilateral arm training: Why and who benefits?", NeuroRehabilitation, vol. 23, No. 1, 2008, pp. 29-41.
Whitall, J., et al., "Repetitive Bilateral Arm Training With Rhythmic Auditory Cueing Improves Motor Function in Chronic Hemiparetic Stroke", Stroke, vol. 31, No. 10, 2000, 6 pages.
Wittenberg, G. F., et al., "Constraint-Induced Therapy in Stroke: Magnetic-Stimulation Motor Maps and Cerebral Activation", The American Society of Neurorehabilitation, 2003, 10 pages.

* cited by examiner

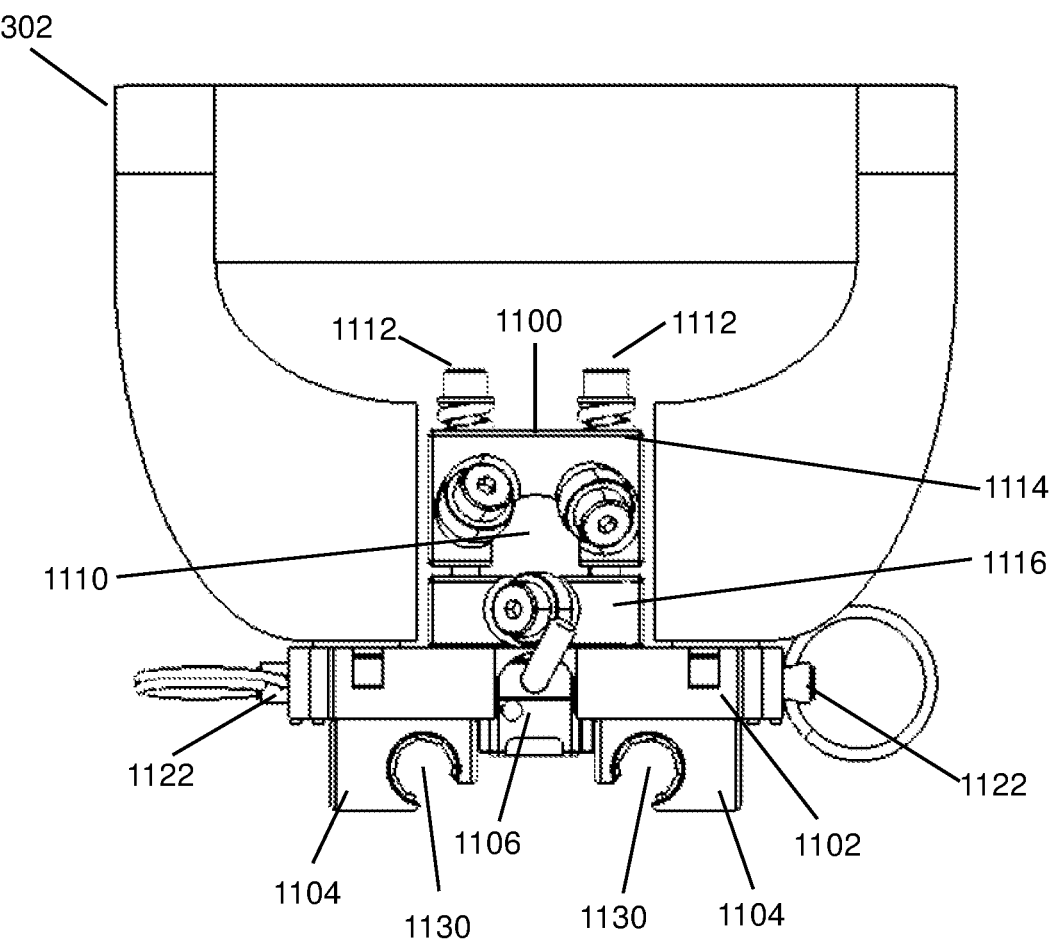
FIG. 11

340

1302

1300

1310

1300

1312

340

1312

1310

1302

1300

1300

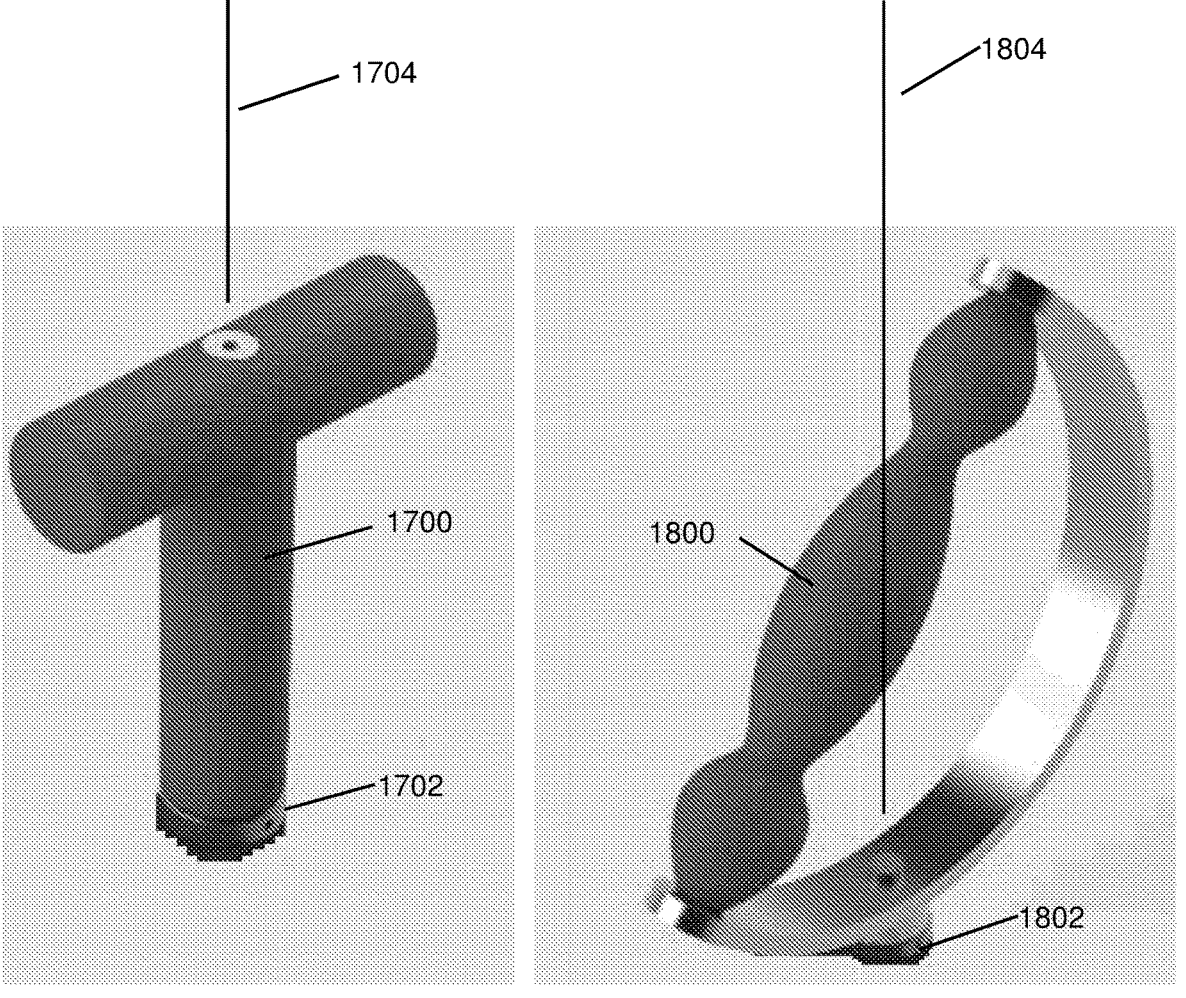
FIG. 17                    FIG. 18

MOBILE STATION 2101

AUTOMATIC ARM TRAINING DEVICE, SYSTEM, AND METHOD

CROSS-REFERENCE TO RELATED APPLICATIONS

This application is a National Stage entry and claims priority to PCT/US2020/065605, filed Dec. 17, 2020, which claims benefit of Provisional Application Ser. No. 62/949,128, filed Dec. 17, 2019, the entire contents of which are hereby incorporated by reference as if fully set forth herein, under 35 U.S.C. § 119(e).

BACKGROUND

Annually, about 800,000 individuals in the US and 17 million worldwide suffer a stroke. Most are left with residual neurological deficits that persistently impair function, making stroke the leading cause for serious disability in developed countries. Meanwhile, prevalence rates in low- and middle-income countries will shortly surpass those of developed nations. Among the most common and disabling deficits is arm hemiparesis as it has been reported as the dominate functional limitation in as much as 80% of patients with acute stroke. Even after patients have left the acute care setting, 50% to 95% of individuals have continued impairment of the upper extremities (UE).

Current widespread care and therapy models focus on unilateral training of the paretic arm and when not successful, resort to learning compensatory techniques with their non-paretic (NP) arm. As a result, the current standard of care is often limited to managing (not resolving) the problem, and relies on the patient learning compensatory skills to make up for their deficit, which may result in further learned disuse What can be important to the stroke survivors is their ability to carry on their daily tasks. Many core activities of daily living (ADL), like dressing, bathing, toileting, and mobility functions like carrying objects, require the use of both arms. Furthermore, aging adults that are more likely to suffer stroke have an increased reliance on both arms to perform their ADL. If most tasks are performed bilaterally in those most likely to suffer a stroke, aging adults, then training should be task specific and thus, bilateral. The focus on task-specificity and bilateral training is supported by distinct neuromotor control mechanisms at play in unilateral versus bilateral UE skills A bilateral arm trainer with rhythmic auditory cuing (BATRAC) apparatus has been shown to improve UE motor function in mild/moderately affected patients well beyond the 3-month period (chronic hemiparesis) after 6 weeks of repetitive non-progressive training. In a randomized study, functional imaging (fMRI) has shown that new foci of contralesional as well as ipsilesional neural activation for paretic arm movement occurs after BATRAC training, but not after dose-matched therapeutic exercises [4].

SUMMARY

BATRAC was used for "no-assist" training only, with no instrumentation for measuring patient performance and only auditory cueing to provide patient stimulus. It is here recognized that adding instrumentation to the BATRAC, to sense patient performance or provide video feedback or both, offers feedback to patients during use to enhance functional outcomes, while also allowing care providers (such as physical therapists, PTs) to track patient progress objectively. Furthermore, instrumenting with assist mechanisms will produce repetitive training without human intervention. Even further, configuring bilateral interaction in both performance and assist is likely to lead to better outcomes. Thus, techniques are provided for arm training that enable and are suitable for automated objective performance assessment or automated repeated or bilateral training or some combination.

In a first set of embodiments, a therapeutic device includes a handle, a sensor assembly, and a display. The handle is configured to move along a path. The sensor assembly is configured to provide a measured time series comprising a plurality of handle location measurements at a corresponding plurality of measured time instances. The display is configured to present an image based on the measured time series.

In some embodiments of the first set, the therapeutic device includes a handle drive assembly secured to the handle and configured to apply position-correcting force to the handle when the measured time series indicates an actual position of the handle which deviates from a target trajectory for the handle by a predetermined tolerance. The handle drive assembly is also configured to apply no position-correcting force to the handle so long as the actual position of the handle is within the predetermined tolerance. In some of these embodiments, the handle drive assembly is configured to be backdriven by the handle only when the position of the handle is within the predetermined tolerance.

In some embodiments with a handle drive assembly, the handle drive assembly includes a position-controlled DC motor secured to the handle via a linkage. In some of these embodiments, the linkage comprises a lead screw secured to the DC motor and a linear actuator configured to convert rotation of the lead screw into translation of the handle.

In some embodiments of the first set, the device includes two handles, one handle for each hand of a user. In some of these embodiments, the device includes two handle drive assemblies, one handle drive assembly for each handle.

In some embodiments of the first set, a system includes the therapeutic device and a processor. The processor is configured to receive from the sensor assembly the measured time series. The processor is also configured to determine an objective metric for the subject based at least in part on deviations of the measured time series from a target trajectory for the subject. Furthermore, the processor is configured to present on the display an image based on the objective metric.

In a second set of embodiments, an automatic method for providing arm training includes receiving first data that indicates a target trajectory, for movement along a path, of a handle configured to be held at a distal end of an arm of a subject. The method also includes, operating a sensor configured to provide a measured time series comprising a plurality of handle location measurements at a corresponding plurality of measured time instances. Still further, the method includes determining an objective metric for the subject based at least in part on deviations of the measured time series from the target trajectory. Even further, the method includes presenting on a display an image based on the objective metric.

In some embodiments of the second set, the first data further indicates a second target trajectory for movement of a different second handle configured to be held at a distal end of a different second arm of the subject. The sensor is further configured to provide a different second measured time series comprising a plurality of second handle location measurements at a second corresponding plurality of measured time instances. The step of determining the objective metric further includes determining the objective metric based at least in part on second deviations of the second measured time series from the second target trajectory.

In some embodiments of the second set, the first data also indicates a tolerance slot bracketing the target trajectory. The step of determining the objective metric includes determining the objective metric based at least in part on deviations of the measured time series from the tolerance slot bracketing the target trajectory. In some of these embodiments, the method also includes operating a drive mechanically connected to the handle to reduce deviations of the measured time series outside the tolerance slot bracketing the trajectory. In some of these embodiments, the step of determining the objective metric includes determining the objective metric based at least in part on said operating the drive.

In some embodiments of the second set, the method includes modifying the target trajectory based at least in part on the objective metric. In some embodiments of the second set, the target trajectory is a curve of minimum jerk for a path of specified range and a cycle of specified period. In some of these embodiments, the method still further includes modifying, based at least in part on the objective metric, at least one of the specified range or the specified period.

In other sets of embodiments, a non-transitory computer-readable medium, or an apparatus, is configured to perform one or more steps of the above method.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 11 is a perspective view of an example embodiment of an actuated slide mount assembly of the therapeutic device of FIG. 3.

FIG. 17 is a perspective view of an alternate example embodiment of the handle.

FIG. 18 is a perspective view of another alternate example embodiment of the handle.

FIG. 21 is a diagram of example components of a mobile terminal (e.g., cell phone handset) for communications, which is capable of operating in the system of FIG. 1A, according to one embodiment.

DETAILED DESCRIPTION

A method and apparatus are described for automated arm training. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of bilateral synchronized assisted repeated movements of a subject's arms, for human subject such as a stroke survivor. However, the invention is not limited to this context. In other embodiments automated single arm training is provided, or arm extension/retraction training is combined with training of arm rotation (wrist, elbow or shoulder, or some combination) for injured or diseased or normal animals, such as apes, or humans. Other embodiments include resistance training (using a position rather than slot controller) for strength related impairments as well as active assistance training (using a position rather than slot controller) for passive stretching exercises in the context of muscle conditioning.

1. Overview 1.1 Structures

Figure 1A:
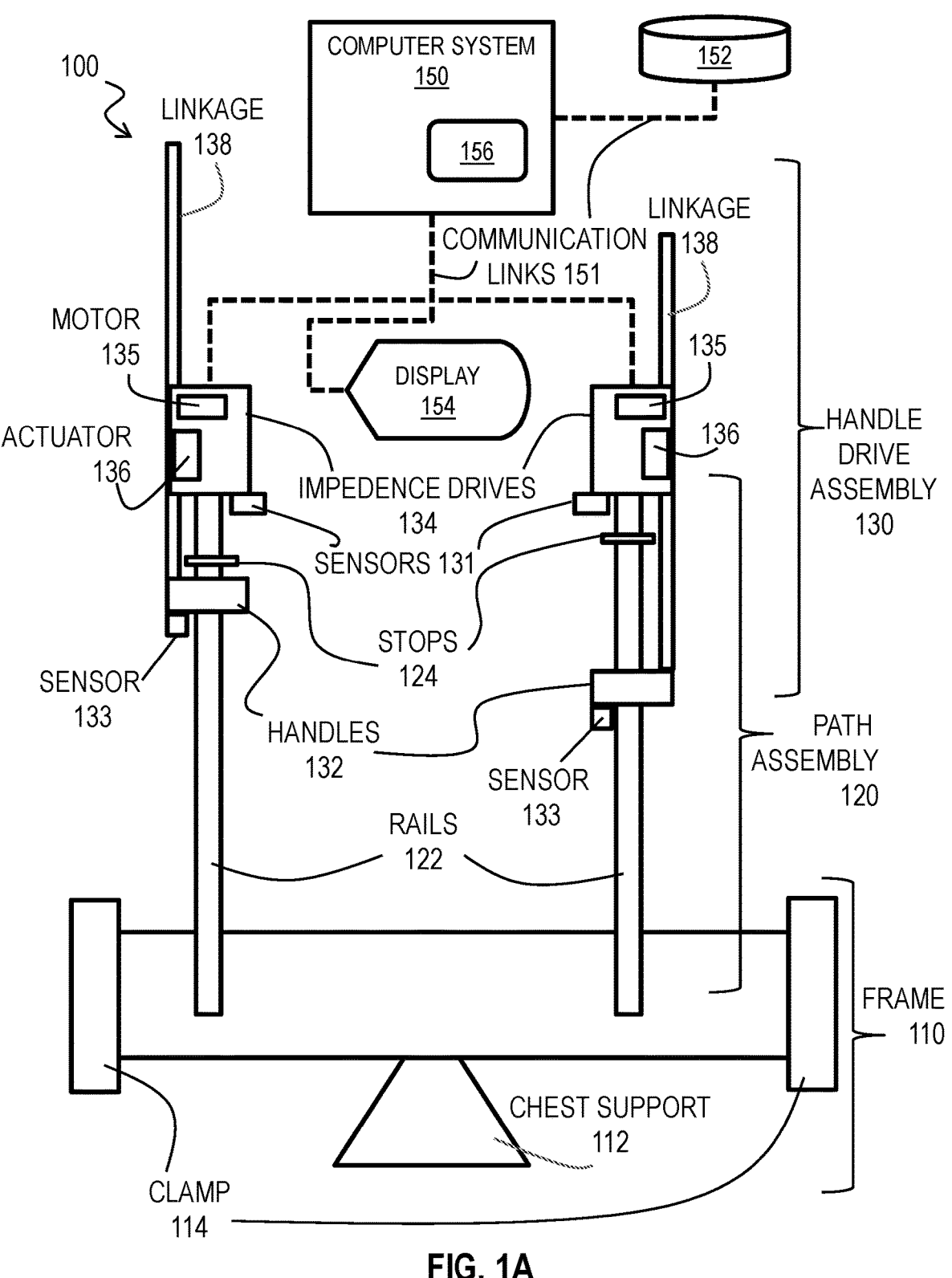
FIG. 1A is a block diagram that illustrates an example system for automated bilateral arm training, according to an embodiment.

FIG. 1A is a block diagram that illustrates an example system 100 for automatic bilateral arm training, according to an embodiment. The system 100 includes a computer system 150 with data structure 152 and display 154 and a therapeutic device comprising a frame 110, a path assembly 120 for each of one or both arms, and a handle drive assembly 130 for each of one or both arms. The frame 110 provides a support structure for the other elements, at least one fastening device, such as clamp 114, to secure to a tabletop or other appropriate horizontal or inclined surface. The frame also includes a chest support 112 to properly space a chest of a subject (not shown) from handles 132 of the apparatus that are part of the handle drive assembly 130, and that are configured to be grasped by a hand or prosthetic at a distal end of an arm of the subject. Any fastener or chest support may be used, including fixed or adjustable structures. Thus, in some embodiments, the system includes a chest support configured to abut a user's chest to hold the user in a proper position relative to the at least one therapeutic device. In an example embodiment, the frame 110, with clamp 114 and chest support 112, is similar to that used in the BATRAC system. In some embodiments, the frame 110 is fixed to the path assembly 120. In some embodiments, the frame 110 is removably attached to the path assembly 120 so that the system 100 is modular, and system components can be disassembled for storage, or shipment, or replacement or repair of damaged parts, or some combination.

The path assembly 120 includes a mechanical path, such as rail 122 and a stop 124, for each arm of the subject. While the path defined by rail 122 depicted in FIG. 1A is straight, in other embodiments the path may be curved or piecewise linear. Each path is configured to allow a handle 132 of the handle assembly 130 to slide along the path, such as rail 122, preventing handle motion perpendicular to the path but offering reduced or negligible resistant to handle movement in the direction of the path. Here negligible resistance is resistance that is imperceptible to the subject. In an embodiment, a lower limit of perceptible is the just noticeable difference (JNF) for force, which is 7% of the reference force. In an embodiment, a maximum achievable impedance is above the human perception of 4.2 N/mm for a "virtual wall." Thus, the system in some embodiments includes a guide rail along which the handle translates, and which defines the path. The stop 124 is configured to prevent the handle 132 from sliding so far from the subject as to cause pain or harm to the subject or interfere with the recovery of the subject, or to prevent having the handle 132 pass a distal end of the path. In various embodiments, the stop 124 is adjustable or removeable or both. Thus, in some embodiments the system includes a stop adjustably positionable along the rail and configured to define an end of the path. In some embodiments, the stop 124 is omitted and the handle drive assembly 130 is configured to prevent the handle 132 from moving too far from a subject positioned at the chest support 112.

When the handle is moved by a subject, the movement of the handle along the path and back to its starting part is called a cycle. A first, or extension, half-cycle is said to begin when the handle 132 is closest to the subject who is propped against the chest support and to end when the handle is farthest from the subject who is still propped against the chest support. A second, or contraction, half-cycle is said to begin when the handle 132 is farthest from the subject who is propped again the chest support and ends when the handle is closest to the subject who is still propped against the chest support. The distance to the handle position at the beginning of the first half cycle and the distance to the handle position at the end of the first half cycle is the cycle range, the distance between those two positions is the cycle extent. The time it takes to complete a half cycle is the half cycle duration. The time it takes to complete both half cycles is the cycle period. A trajectory is a trace of the time dependent position of a handle over one cycle. A target trajectory is a trace of the time dependent position of a handle over one cycle that is desired for a particular patient for therapeutic results; and can be defined by a curve type, a cycle period (or two equal or unequal half-cycle durations) and a cycle extent (or range). In some embodiments, the curve type is a smooth curve, such as a minimum jerk curve. In some embodiments, the curve type is a curve fit to the trajectories of many healthy persons serving as subjects for the system 100, which may be normalized by extent and period.

In some embodiments, the rail 122 is a bar or beam around which the stops 124 and at least a shoe portion of the handle 132, or both, fits. In some embodiments, the rail is an elongated groove or recess in a plank into which the stop 124 or the shoe of the handle 132, or both, fits. In general, the handle 132 is constrained to follow a certain mechanical path such as defined by rail 122. In some embodiments, the system 100 is used for only one arm of the subject and includes only one rail 122 and stop 124. For example, in some embodiments, a rail 122 for an arm not included in training is removed from a modular arrangement of the system 100.

The handle drive assembly 130 includes at least a sensor 131 and the handle 132 that is configured to interface with the path such as rail 122, as described above. Each handle 132 is also configured to be grasped by a hand or prosthetic at a distal end of a corresponding arm of the subject. In various embodiments, the handle 132 has an angled grip that is configured by form or adjustment for grasping by the hand or prosthetic of the subject to cause the arm of the subject to assume a preferred orientation.

The sensor 131 is configured to determine the position of the handle 132 along the path, such as along rail 122. In some embodiments, one sensor 131 is configured to detect the positions of both handles 132 on their corresponding paths, such as rails 122. In some embodiments, there is a separate dedicated sensor 131 for each handle 132, as depicted in FIG. 1A. Thus, in some embodiments, the sensor 131 includes a first sensor configured to provide a first measured time series and a different second sensor configured to provide the second measured time series. In some embodiments, the sensor is based on a time of flight of a light or laser beam or accelerometers or linear encoders, or some combination. Linear encoders include optical and magnetic, and incremental and absolute. In some embodiments, the sensor detects movement of a linkage 138 mechanically connecting the sensor 131 to the handle 132, such as by counting revolutions of a thread engaged with a threaded linkage 138. The sensor 131 is connected by wired or wireless, direct or networked, communication links 151 to computer system 150 which can accumulate and analyze the data from the sensor 131, as described in more detail below. Thus, the system 100 includes a sensor assembly configured to provide a measured time series comprising multiple handle location measurements at a corresponding multiple measured time instances. The sensor 131 provides the advantage of measurements that allow the computer system 150 to produce objective quantified metrics of subject performance, and, in some embodiment, allows the system 100 to adapt an automatic assist tailored to particular needs or goals of a subject. Example embodiments may also include force sensors 133 on the handle for grasp function training.

In some embodiments, which provide an automated assist to a subject, the system 100 includes an impedance drive 134 connected by a different or the same mechanical linkage 138 to the handle 132. The impedance drive 134 includes a motor 135 and an actuator 136; and is under the control of computer system 150 via communication links 151 and provides feedback to the computer system 150 by the same or different communications links 151. The motor 135 provides movement; and the actuator 136 transfers movement from the motor to a force applied along the mechanical linkage 138 to the handle 132. The actuator 136 also serves to transfer force supplied by the subject to a signal that is transferred to computer system 150, e.g., for back driving the impedance drive 134. In various embodiments, each impedance drive 134 has low intrinsic end-point impedance, low inertia (0.6 to 1.5 kilograms), low friction (0.5 to 1.1 Newtons), and is capable of producing a predetermined range of forces (0 to 45 Newtons) and impedances (0 to 2 Newtons/millimeter). In an example embodiment, there may be two 16-bit virtual absolute encoders for position and velocity measurements (higher torques can be produced for limited periods of time). There may also be DC-tachometers with a sensitivity of 1.8 V/rad/sec for redundant velocity sensing. A six degrees-of-freedom force sensor may be mounted on the robot end-effector (e.g. handles 132).

In various embodiments, the handle drive assembly 130 is configured to be imperceptible, or barely-perceptible, to the subject when the actual position of handle 132 is within tolerance of a target trajectory for movement of the handle by the subject. Simple Impedance Control (SIC) renders a device a passive physical system, hence making it immune to contact instability. SIC also explicitly modulates the end-effector mechanical impedance rather than position (or force), which for the patient, translates to "robot feel". Coupled with highly back-drivable actuators (gearless, linear screw drives rendering negligible stiction), a robot can be made to "get out of the way" when desired, and the patient does not expend effort to learn robot dynamics, which is the case for many commercial robotic arm trainers. SIC, along with a damping controller, is utilized as a one dimensional (1-D) moving box or "slot" controller, in which a virtual slot is created around each point of a virtual reference, called herein a target trajectory. In some embodiment the virtual reference is a minimum jerk trajectory that has been experimentally verified.

The target trajectory can be for one arm, or for both arms moving together (in phase), or for both arms moving in opposition (180 degrees out of phase), or for any other coordinated movement of two arms (out of phase by different amounts). Such imperceptible, or barely-perceptible force is accomplished by allowing the subject to be able to backdrive the impedance drive 134. When the impedance drive 134 provides reduced or no assistance, the subject applies force to exert the control on the handle 132; and, this may accelerate therapeutic progress. In some embodiments, the impedance-drive 134 is configured to apply viscous cushioning when the actual position of the handle 132 is within the tolerance of the target trajectory. This offers an advantage in possibly inducing fine motor skill recovery in the subject.

In various embodiments, when the subject's movements are within the slot (e.g., the subject is backdriving the motor-actuator assembly), there are no assistive or resistive (viscous) forces applied. In contrast, when the subject's movements are outside the slot, the Simple Impedance Controller (SIC) provides safe and gentle "push" (if the subject is "behind" the lower edge of slot) or "pull" (if the subject is "ahead" of the upper edge of slot) to the handle 132/subject. Safety is assured by using SIC (consisting of a virtual, programmable stiffness and programmable damping that define the commanded controller impedance) since it renders the coupled system passive at the port of interaction; gentle behavior is assured by using backdrivable hardware. In other words, a force field is created around the dynamic slot. The magnitude and phase of this force field are dependent on the controller parameters. The slot (or moving box) control strategy is versatile in that, arbitrary control laws within and/or outside the slot can be programmed. For example, in some embodiments one may choose to have the device provide viscous damping if the subject's movements are outside the slot, and no assistance inside the slot. Such a strategy would convert the "assist as-needed" functionality to a "resist as-needed" strategy for strengthening applications.

A virtual tolerance slot brackets the virtual target trajectory. The top and bottom edges of the slot move continuously such that they pseudo-collapse at the end of the movement. At any given time, if the actual (hand) position is outside the slot, assistance is provided in accordance with SIC dynamics—the magnitude depends on both the controller gains and the positional and velocity error, while the directionality ("push" or "pull") depends only on the latter. Inside the slot however ("on task"), the hand experiences no positional assistance; instead, it experiences viscous cushioning in accordance with the dynamics of a damping controller. This strategy provides two critical benefits: 1. Spatial Autonomy, wherein the patient receives (or not) assistance if the movement is conformant with the needs of the task (or not); and 2. Temporal Autonomy, wherein due to the continually diminishing height of the slot, the amount of spatial autonomy reduces over time in order to "hold" the gains made over the course of the movement. Mechanistic studies utilizing the MIT-Manus in chronic stroke show that recovery in arm motor control occurs via the blending of sub-movements, eventually resulting in a continuous blended movement well modeled by a minimum jerk trajectory. Thus, when the actual position of handle 132 is outside of the tolerance of the target trajectory, the impedance drive 134 is configured to exert corrective force on the handle 132, thus "assisting" the subject. For example, the arm training module 156 is further configured as a simple impedance controller (SIC) with a programmable reference position (target trajectory), proportional gain (controllable torsional stiffness), and a derivative gain (controllable torsional damping in parallel with the stiffness).

Thus, in some embodiments, the system 100 includes a handle drive assembly 130 secured to the handle 132 and configured to apply position-correcting force to the handle 132 when the measured time series indicates an actual position of the handle which deviates from target trajectory for the handle by a predetermined tolerance, and is configured to apply no position-correcting force to the handle 132 so long as the actual position of the handle 132 is within the predetermined tolerance. In addition, as described above, in some embodiments, the handle drive assembly 130 is configured to be backdriven by the handle 132 only when the position of the handle 132 is within the predetermined tolerance. Further, in some embodiments, as described above, the handle drive assembly 130 is configured to apply viscous cushioning to the handle so long as the actual position of the handle 132 is within the predetermined tolerance.

The hardware components, including frame 110, path assembly 120, and handle drive assembly 130, together constitute a therapeutic device, as that term is used herein. In a modular version of the therapeutic device, the handle 132, impedance drive 134 or sensor 131, or some combination, is configured to be separated from the mechanical path, such as rail 122, or the path assembly from the frame 110, or some combination, for separate storage, shipment, repair or replacement, or some combination of reasons.

The computer system 150 includes a display 154, a data structure 152, and an arm training module 156 configured to perform one or more steps of a method described in more detail below with reference to a flow diagram depicted in FIG. 2A. The module 156 is in communication with data structure 152 and display 154 via one or more communications links 151, which, as indicated above, may be wired or wireless, direct or networked. In some embodiments, computer system 150 includes multiple different processors serving as different hosts in a local or global network. The display 154 is configured to be viewed by the subject in order for the system 100 to provide feedback on progress based at least in part on the sensor measurements, or motivation to improve performance, or both. Thus, the system includes a display configured to present an image based on the measured time series. In some embodiments, the display 154 is a video display. In some embodiments, audio presentations are also provided by display 154, e.g., to provide feedback and motivation to a vision-impaired subject. In some embodiments, a computer system of FIG. 19, or a chip set of FIG. 20 serves as computer system 150. In some embodiments, all elements of the computer system are in an integrated device, such as a desktop computer, or a mobile device, such as a tablet or cell phone (the latter depicted e.g., in FIG. 21).

In various embodiments, the arm training module 156 is configured to automatically receive first data from a caregiver, either directly through a graphical user interface (GUI) or other input device, or indirectly from data structure 152, at least about a target trajectory for a particular subject. Furthermore, the based on the movements detected by sensors 131 the training module is configured to produce one or more objective metrics of subject performance relative to the target trajectory; and, optionally record the data or objective metric or both in data structure 152. In some embodiments, the arm training module 156 is also configured to control the impedance drives 134, if any, based on subject performance. In addition, the arm training module 156 is also configured to provide feedback or motivation or both to the subject through display 154, and to provide at least one objective metric to a caregiver for the subject, either via the display 154 or by a message transmitted to a device used by the caregiver, and optionally to update the target trajectory based on subject performance. The caregiver is then enabled to treat the subject based on the at least one objective metric. In some embodiments, the treatment includes prescribing a number of sessions on the system 100 for the subject and one or more adjustments to the target trajectory for one or more such sessions. Thus, the system includes a processor configured to receive from the sensor assembly the measured time series; determine an objective metric for the subject based at least in part on deviations of the measured time series from a target trajectory for the subject; and, present on the display an image based on the objective metric.

For example, in some embodiments, in addition to auditory cueing, visual cueing can be equally or more effective, especially in providing performance-based patient feedback for motivation and goal-setting, which are fundamental to motor learning. Visual tasks e.g., video games, are integrated with rehabilitation techniques to also tackle patient nonadherence. Physiological data suggests that game play can induce neuro-plastic reorganization that leads to long-term retention and transfer of skill. Studies have been conducted to evaluate the efficacy of incorporating a visual task to aid neurorehabilitation, robot-assisted or otherwise. There is evidence suggesting that key factors in game design, including choice, reward, and goals, lead to increased engagement. For example, early clinical trials with an ankle training robot, Anklebot, consisted of subjects playing a "racer" video game (described in more detail below with reference to FIG. 2F) as a part of a seated, performance-based training protocol. In some embodiments, machine learning algorithms dynamically auto-adjust specific videogame parameters (e.g., wall speed and gate location based on trajectory curve type, range and period) based on ongoing improvement or decline in the patient's inter- or intra-session performance.

Figure 1B:
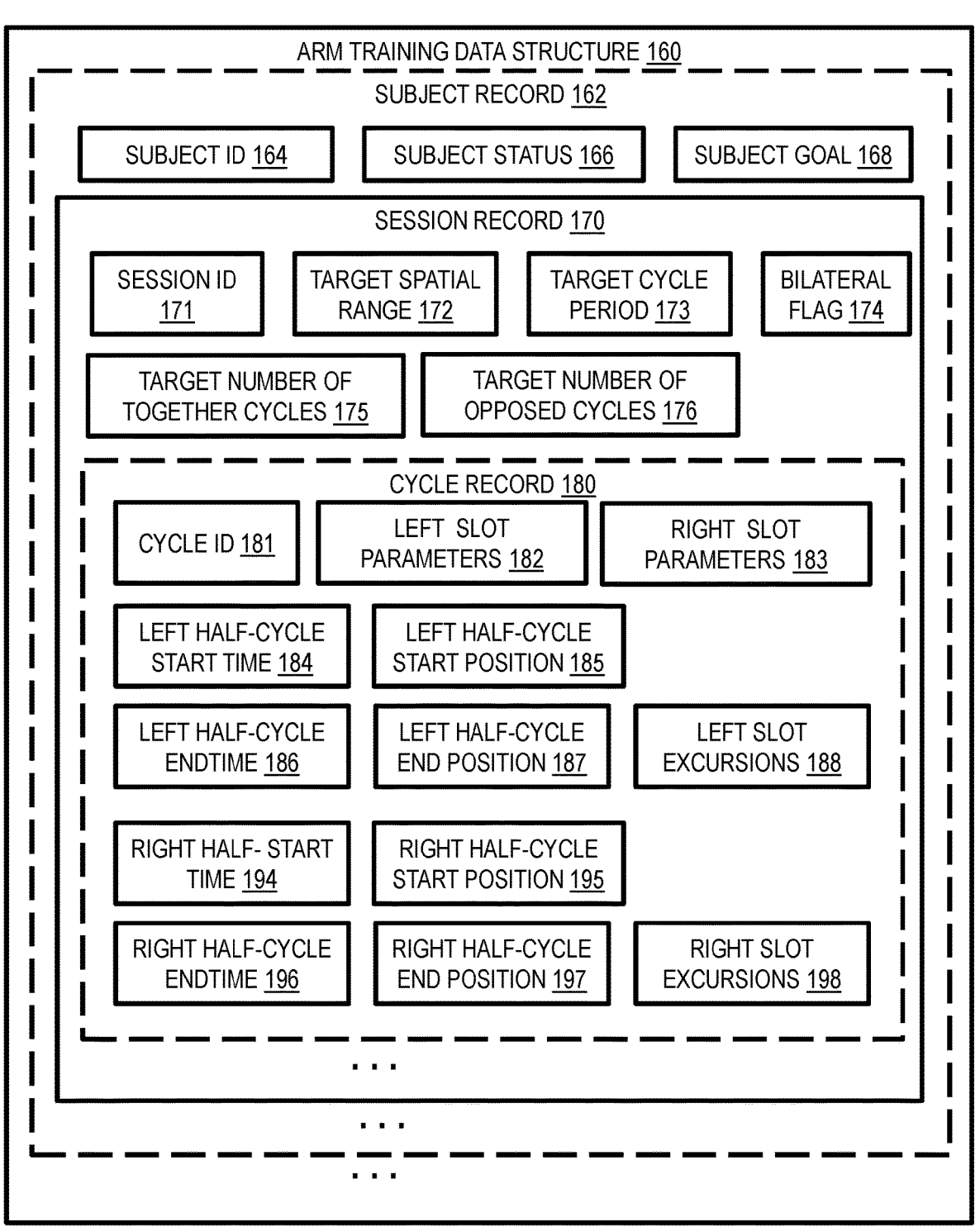
FIG. 1B is a block diagram that illustrates an example data structure for automated bilateral arm training, according to an embodiment.

FIG. 1B is a block diagram that illustrates an example data structure 160 for automated arm training, according to an embodiment. Data structure 160 is one example of data structure 152. The data structure 160 includes a record for each subject, indicated by subject record 162 (dashed outline) among other subject records for other subjects indicated by ellipsis inside data structure 160 and outside subject record 162.

Each subject record 162 includes a subject identifier (ID) field 164, a subject status field 166, a subject goal field 168, and a session record 170 (solid outline) among zero or more other session records for other sessions by this subject indicated by ellipsis inside subject record 162 and outside session record 170. The subject ID field 164 holds data that indicates a unique identifier for the subject, such as government issued ID like a Social Security Number (SSN), a name and birthdate, a unique or random number generated by a clinic or by system 100 itself, and used as a key in a secured database for storage of private or encrypted information. The subject status field 166 holds data that indicates current status of the subject with respect to the use of the system 100, such as a current trajectory for one or both arms or a current or average score for an objective metric achieved over one or more current or previous sessions, or both. The subject goal field 168 holds data that indicates a trajectory or score or both for the subject to complete therapy, such as a target trajectory with its corresponding curve type, range and durations.

Each session record 170 includes a session identifier (ID) field 171, a target spatial range field 172, a target cycle period field 173, a bilateral flag field 174, a target number of together cycles field 175, and a target number of opposed cycles field 176. Each session record 170 also includes a cycle record 180 (dashed outline) among zero or more other cycle records for other cycles for this session, indicated by ellipsis inside session record 170 and outside cycle record 180. The session ID field 171 holds data that indicates a unique identifier for the session, at least for the current subject, such as a session sequence number. The target spatial range field 172 holds data that indicates the cycle range or extent or curve type or some combination for a target trajectory for the session; and, the target cycle period field 173 holds data that indicates a period or first half cycle duration or second half cycle duration or some combination for the target trajectory for the session. In some embodiments, either of field 172 or field 173 also holds data that indicates not only the target trajectory values, but a tolerance slot in space or time for differences in the actual trajectory of a handle that do not invoke a scoring penalty or robotic assist or both.

The bilateral flag holds data that indicates whether the training is for one arm (e.g., flag bit value equal to 1) or both arms (e.g., flag bit value equal to 0). In some embodiments, the bilateral flag is two bits, e.g., the first bit indicating whether the left arm is included (0→no, 1→yes) and the second bit indicating whether the right arm is included (0→no, 1→yes). The target number of together cycles field 175 holds data that indicates how many cycles are in the session (either planned or completed). If the bilateral flag indicates both arms are undergoing training, then the number indicated in field 175 is the number of cycles in which the arms are moving together (in phase). The target number of opposed cycles field 176 holds data that indicates how many cycles in the session (either planned or completed) have the arms moving in opposite directions if the bilateral flag indicates both arms are undergoing training. In some embodiments, the out-of-phase phase difference is understood to be 180 degrees as arms move opposite to each other. In other embodiments, the field 176 also holds data that specifies a phase difference and the number of cycles, for each of one or more different out-of-phase trajectories. If the bilateral flag indicates only one arm is undergoing training then, field 176 may be omitted.

Each cycle record 180 holds data collected by sensor 131 during one cycle of the session, which is used to determine various metrics or target trajectories or some combination. The cycle ID field 171 holds data that indicates a unique identifier for the cycle or half-cycle, at least for the current session, such as a half cycle sequence number. The left slot parameters field 182 holds data that indicates an envelope of trajectories for the subject's left arm that do not invoke a scoring penalty or robotic assist or both. For example, the field 182 holds data that indicates a distance ahead of, or behind, the target trajectory at a particular instant of the current cycle that will not invoke a scoring penalty or robotic assist or both. In some embodiments, the field 182 also includes current values for the target trajectory that may be different from the session target trajectory indicated in session fields 172 or 173 or both. Similarly, the right slot parameters field 183 holds data that indicates an envelope of trajectories for the subject's right arm that do not invoke a scoring penalty or robotic assist or both. In some embodiments, at one or more cycles, differences from session target and slot trajectories are not allowed; and, then fields 182 or 183 or both can be omitted.

Left half-cycle start time field 184 holds data, such as a timestamp, that indicates an instant when the left handle begins to be moved by the subject from the nearest or farthest point (for either the extension or contraction half-cycles, respectively). Left half-cycle start position field 185 holds data, such as a time of flight or number of rotations or distance, that indicates a location where the left handle begins to be moved by the subject from the nearest or farthest point (for either the extension or contraction half-cycles, respectively). Left half-cycle end time field 186 holds data, such as a timestamp, that indicates an instant when the left handle moved by the subject reaches the farthest or nearest point (for either the extension or contraction half-cycles, respectively). Left half-cycle end position field 187 holds data, such as a time of flight or number of rotations or distance, that indicates a location where the left handle moved by the subject reaches the farthest or nearest point (for either the extension or contraction half-cycles, respectively). The left slot excursion field 188 holds data that indicated occurrences of handle position outside the slot tolerances of the target trajectory, such as the number of positive excursions (too far ahead) or negative excursions (too far behind) or number of total excursions or average positive or negative excursion distance or time or variance thereof or some combination. In some embodiment, field 188 holds all the left handle measurements in the half-cycle as a time series.

Similarly, right half-cycle start time field 194 holds data, such as a timestamp, that indicates an instant when the right handle begins to be moved by the subject from the nearest or farthest point (for either the extension or contraction half-cycles, respectively, if arm motions are in phase or the opposite if arm motions are out of phase). Right half-cycle start position field 195 holds data, such as a time of flight or number of rotations or distance, that indicates a location where the right handle begins to be moved by the subject from the nearest or farthest point (for either the extension or contraction half-cycles, respectively, if in phase or the opposite if out of phase). Right half-cycle end time field 196 holds data, such as a timestamp, that indicates an instant when the right handle moved by the subject reaches the farthest or nearest point (for either the extension or contraction half-cycles, respectively, if in phase or the opposite if out of phase). Right half-cycle end position field 197 holds data, such as a time of flight or number of rotations or distance, that indicates a location where the right handle moved by the subject reaches the farthest or nearest point (for either the extension or contraction half-cycles, respectively, if in phase or the opposite if out of phase). The right slot excursion field 198 holds data that indicates occurrences of handle position outside the slot tolerances of the target trajectory, such as the number of positive excursions (too far ahead) or negative excursions (too far behind) or number of total excursions or average positive or negative excursion distance or time or variance thereof or some combination. In some embodiment, field 198 holds all the right handle measurements in the half cycle as a time series.

Timestamp temporal resolution on the order of one millisecond to 100 milliseconds is beneficial. Position resolution on the order of 0.1 millimeter to 10 millimeters is beneficial. If the left arm is not undergoing training, then any or all fields 182, 184, 185, 186, 187, 188 can be omitted. If the right arm is not undergoing training, then any or all fields 183, 194, 195, 196, 197, 198 can be omitted.

Although processes, equipment, and data structures are depicted in FIG. 1A and FIG. 1B as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

1.1 Method

Figure 2A:
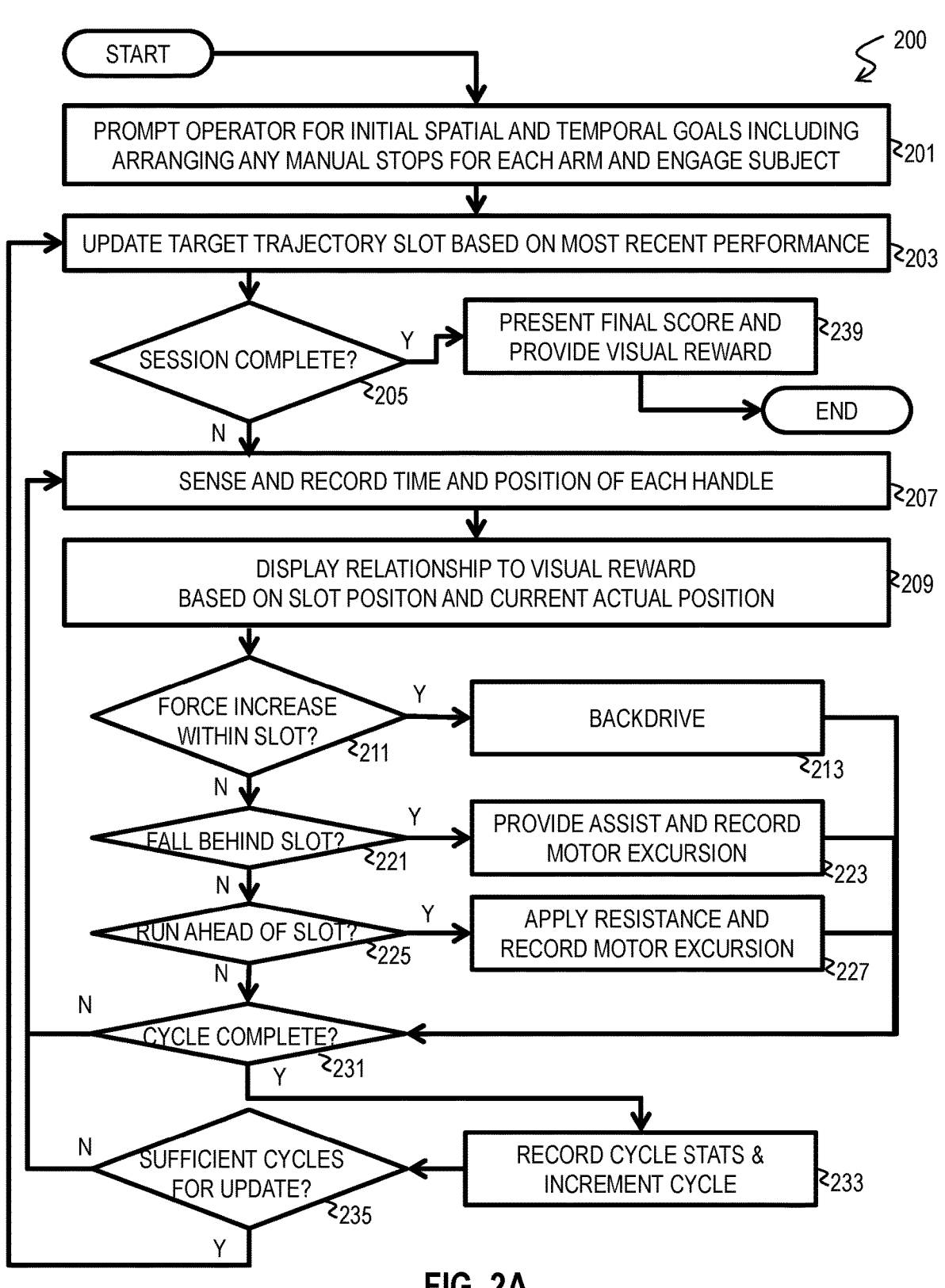
FIG. 2A is a flow diagram that illustrates an example method to operate the system of FIG. 1A for arm training, according to an embodiment.

FIG. 2A is a flow diagram that illustrates an example method to operate the system 100 of FIG. 1A for automated arm training, according to an embodiment. Although steps are depicted in FIG. 2A as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 201, an operator, also called a user herein, such as a caregiver for a subject such as a human patient, is prompted to configure system 100 for the particular subject. For example, a graphical user interface is presented at display 154 with active area configured to allow the operator to enter data that indicates the subject and a goal for that subject, such as a target trajectory defined by a trajectory curve type, a cycle range, and a cycle period for one or both arms. For example, the data can entered using a pointing device 1916 or other input device 1913 depicted in FIG. 19 on computer system 1900. The subject can be identified in any way suitable for populating subject ID field 164. In some embodiments, the subject ID is stored in field 164, and the target trajectory stored in field 168, of subject record 162 for the current subject. Thus, the method includes receiving first data that indicates a target trajectory for movement along a path, for a handle configured to be held at a distal end of an arm of a subject. Further, in some embodiments, the first data also indicates a second target trajectory for movement of a different second handle configured to be held at a distal end of a different second arm of the subject. In some configurations, such as when both arms are equally capable, the two target trajectories may be the same.

In some embodiments, the operator is also prompted to manually position any stops 124 for any paths such as rails 122, for one or both arms. The operator may also be prompted to position the subject against the chest support 112 and position the subject's arms so that a hand or prosthetic at a distal end of each arm to be trained grasps a corresponding handle 132. In some embodiments, positioning the subject's arm may involve strapping or otherwise attaching a handle to the distal end of the arm.

Figures 2B, 2C:
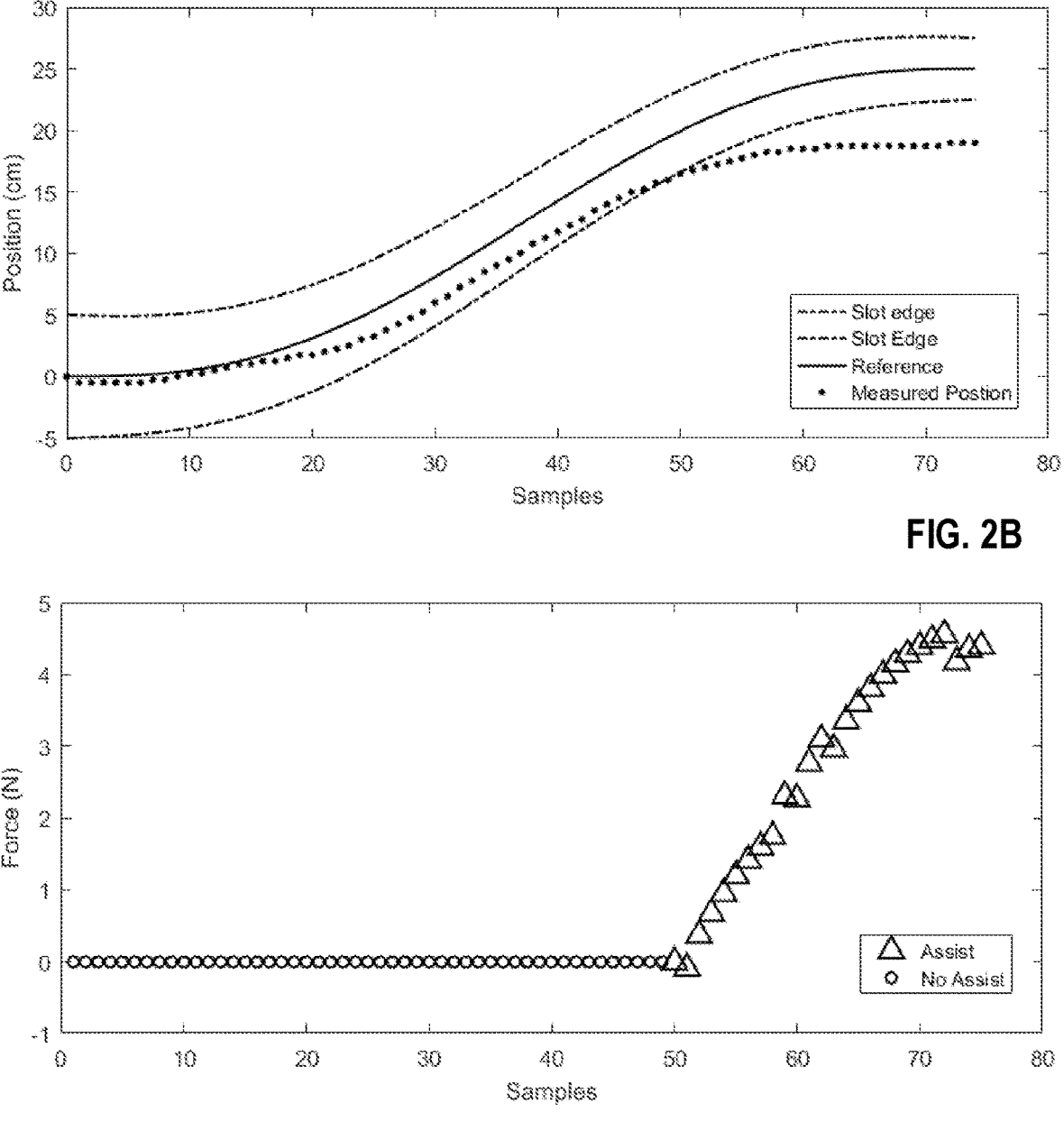
FIG. 2B is a plot that illustrates an example target trajectory for arm movement during a half-cycle with tolerances that define a training tolerance slot and simulated subject arm movement, according to an embodiment.
FIG. 2C is a plot that illustrates example forces applied by an impedance drive in response to the simulated arm movements depicted in FIG. 2B, according to an embodiment.

Indicating the target trajectory goal in field 168 includes defining a tolerance slot for the training, such that if the subject performance is within the tolerance slot, no scoring penalty or, if available, no robotic assistance will be called upon or applied. FIG. 2B is a plot that illustrates an example target trajectory for arm movement during a half-cycle with tolerances that define a training tolerance slot and simulated subject arm movement, according to an embodiment. The horizontal axis indicates elapsed time in units of time samples; and, the vertical axis indicates distance from a handle position on the path closest to the subject in units of centimeters. The solid trace indicates a target trajectory for a half-cycle with a cycle range from 0 centimeters to 10 centimeters, and a half-cycle duration of 100 time samples. The curve type is continuous with continuous first and second temporal derivatives starting at zero for both velocity and acceleration, reaching a maximum acceleration at about 20 time samples and reducing acceleration to zero at a maximum velocity by about 40 time samples, and beginning to decelerate at about 60 time samples, reaching a maximum deceleration at about 80 time samples, and coming to a graceful stop with zero velocity and zero deceleration at 10 cm range and 100 time sample duration. Certain curves with constraints on maximum acceleration and maximum deceleration are called "no jerk" curves. (An example of a reference trajectory that is not the minimum jerk, or smoothest, trajectory is ramp up-hold-ramp-down-positional profile. Slots can be created around such a trajectory in a manner identical to the minimum jerk trajectory. A benefit of using the mathematical model of the minimum jerk trajectory for the reference is that it has been experimentally validated in humans, e.g., experimental trajectories for point-to-point goal oriented planar movements made by nondisabled individuals match with the theoretical minimum jerk positional profiles.) The same curve type can be used with a different half-cycle range or different half-cycle duration or both. In some embodiments, the cycle is completed with a return half-cycle that can use the same or different curve and same or different half-cycle range and the same or a different half-cycle duration.

The dot-dashed lines indicate the tolerance limits, called herein a tolerance slot, for the subject to proceed near the target trajectory without penalty or robotic assist. At a given time sample, the tolerance slot in the illustrated embodiment can be viewed as any position lying between a position one centimeter ahead of the target trajectory at that time sample and one centimeter behind the target trajectory at that time sample. Equivalently, at a given position, the tolerance slot in the illustrated embodiment can be viewed as any time occurring between a time 5 time samples before of the target trajectory at that position and a time 5 time samples after the target trajectory at that position. In other embodiments other tolerances are used. In some embodiments, the tolerances are small, such as about equal to the measurement error of the spatial sensor and timestamp clock; and almost any deviation will be an excursion outside the slot. In some embodiments, the range tolerance slot reduces to zero at the half-cycle range ends. Thus, in some embodiments, the first data further indicates a tolerance slot bracketing the target trajectory. The points plotted in FIG. 2B are simulated measurements from sensor 131 of handle position as moved by a subject with some jittery movement impairment provided for the purposes of illustration.

Returning to FIG. 2A, in step 203, the target trajectory and tolerance slot, e.g., as stored in subject status field 166, or subject goal field 168, or session spatial range field 172, or session cycle period 173, or cycle left slot parameters field 182, or right slot parameters field 183, or some combination, are updated based on any recent measurements by sensor 131 of handle movement effected by the subject and indicative of the subject performance ability, as described in more detail below. If there are no new measurements, such as before the session begins, step 203 is skipped.

In step 205, it is determined whether the session is complete. If so, control passes to step 239 described below. If not, such as when the session is beginning, control passes to step 207.

In step 207 data is received from the sensor during a cycle of the session, and the time and position of each handle is recorded, e.g., in fields 188 for the left handle and 198 for the right handle for every sample time in the half-cycle. Thus, the method includes operating a sensor configured to provide a measured time series comprising a plurality of handle location measurements at a corresponding plurality of measured time instances. In some embodiments, only excursions outside the tolerance slot are recorded, e.g., as the number of excursions or the number in each direction or the number and sum and sum of squares of excursions in each direction so that statistics of excursions can be computed. For example the number of excursions, the average excursion, the number of positive excursions, the average positive excursion, the number of negative excursions, the average negative excursion, the excursion variance can all be computed and any used as an objective metric. In addition, a weighted sum of any or all of these individual measures can provide a single-valued score that serves as the objective metric. Even if there are no excursions, the maximum range and shortest cycle period to accomplish excursion free motions can each be an objective measure or contribute to a single-valued score. Thus, the method includes determining an objective metric for the subject based at least in part on deviations of the measured time series from the target trajectory. In some embodiments, the sensor is further configured to provide a different second measured time series comprising a plurality of second handle location measurements at a second corresponding plurality of measured time instances. In these embodiments, determining the objective metric further comprises determining the objective metric based at least in part on second deviations of the second measured time series from the second target trajectory.

In step 209, the deviations from the target trajectory, such as the excursions outside the tolerance slot, along with the relationship to the target trajectory, are presented on display 154. Thus, in some embodiments, determining an objective metric involves determining the objective metric based at least in part on deviations of the measured time series from the tolerance slot bracketing the target trajectory. In some embodiments, the presentation is literally the target trajectory and the measured positions, such as depicted in FIG. 2B, with the points representing the actual performance by the subject. However, this information is diffuse and both difficult and time consuming to process, especially while the subject is concentrating on performing the arm motion tasks or the caregiver is juggling the needs of multiple patients. Thereof, in some embodiments, a more intuitive presentation suitable to provide feedback and motivation to the subject and a quick assessment for use by the caregiver is displayed, such as if the subject were playing a video game.

FIG. 2D through FIG. 2G are block diagrams that illustrate elements of example graphical user interfaces (GUIs) to provide video game-like feedback and motivation for a subject during automated bilateral arm training, according to various embodiments. A graphical user interface is a display screen that includes one or more active areas that allow a user to input data or to operate on data. As is well known, an active area is a portion of a display to which a user can point using a pointing device (such as a cursor and cursor movement device, or a touch screen) to cause an action to be initiated by the device that includes the display. Well known forms of active areas are stand alone buttons, radio buttons, check lists, pull down menus, scrolling lists, and text boxes, among others. Although areas, active areas, windows and tool bars are depicted in FIG. 2D through FIG. 2G as integral blocks in a particular arrangement on particular screens for purposes of illustration, in other embodiments, one or more screens, windows or active areas, or portions thereof, are arranged in a different order, are of different types, or one or more are omitted, or additional areas are included or the user interfaces are changed in some combination of ways.

Figures 2D, 2E:
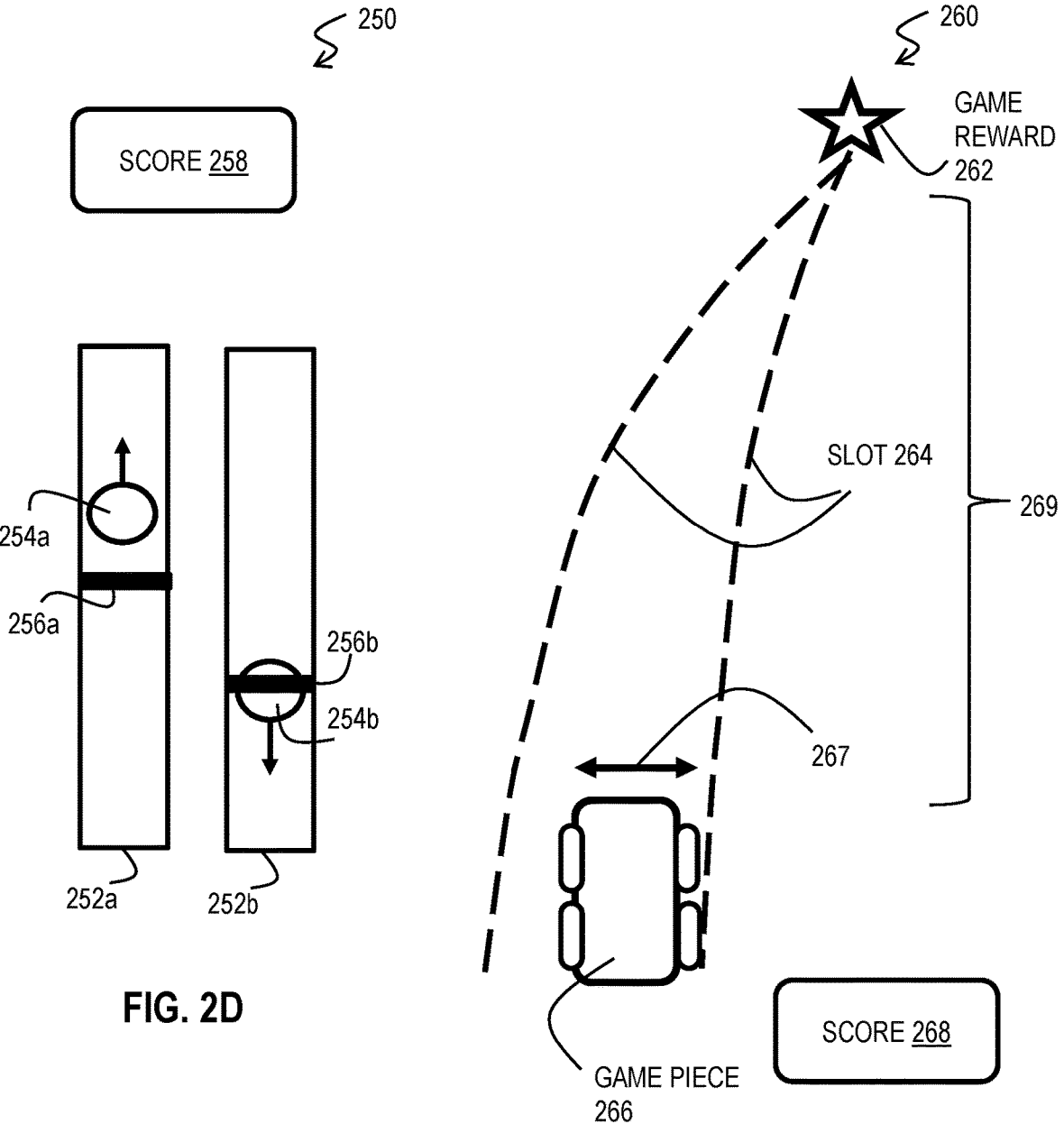
FIG. 2D through FIG. 2G are block diagrams that illustrate elements of example graphical user interfaces (GUIs) to provide video feedback and motivation for a subject during automated arm training, according to various embodiments.

In FIG. 2D, a GUI or other video presentation 250 includes two vertical tracks, track 252a and track 225b, for the left and right arm, respectively, collectively termed tracks 252. On each track is displayed the instantaneous tolerance slot 254a for the left arm and tolerance slot 254b for the right arm, collectively called slots 254, by an extended geometric shape, such as a circle, each moving according to the target trajectory as indicated by an attached arrow. Also displayed is a current position 256a of the left handle and current position 256b of the right handle, collectively called handle positions 256, each represented with a second narrow shape, such as a solid horizontal bar. In this video game interface, the object of the game is to keep the horizontal bar for each arm's handle position 256 in the corresponding slot 254. The degree to which this is done contributes to a score displayed in score area 258. The score is based on a single metric that is a weighted sum of one or more other objective metrics or statistics, as described above. In some embodiments the score decreases with improved performance, as the excursions decrease in number and size. In some embodiments, the score is inversely related to the number and size of the excursions, and thus the score increases as those excursion metrics decrease. The video game and scoring mechanisms provide not only feedback but reward and motivation to the subject.

In FIG. 2E, a video presentation 260 includes a road with left and right edges marked by dashed lines representing the tolerance slot 264. The object of the game is to drive a game piece 266 to a game reward 262 represented by a star at the end of the road. The current position of the left handle and the current position of the right handle control the left and right position of the game pieces 266 as indicated by left-right arrow 267. The distance to the game reward indicated by bracket 269 represents the session time remaining. The object of the game is to keep the game piece 266 on the road by properly moving the left and right handles, and to continue until the game reward is reached. The degree to which this is done contributes to a score displayed in score area 268. As in the game example of FIG. 2D, the score is based on a single metric that is a weighted sum of one or more other objective metrics or statistics, as described above. In some embodiments the score decreases with improved performance; and, in other embodiments the score increases with improved performance.

Figure 2F:
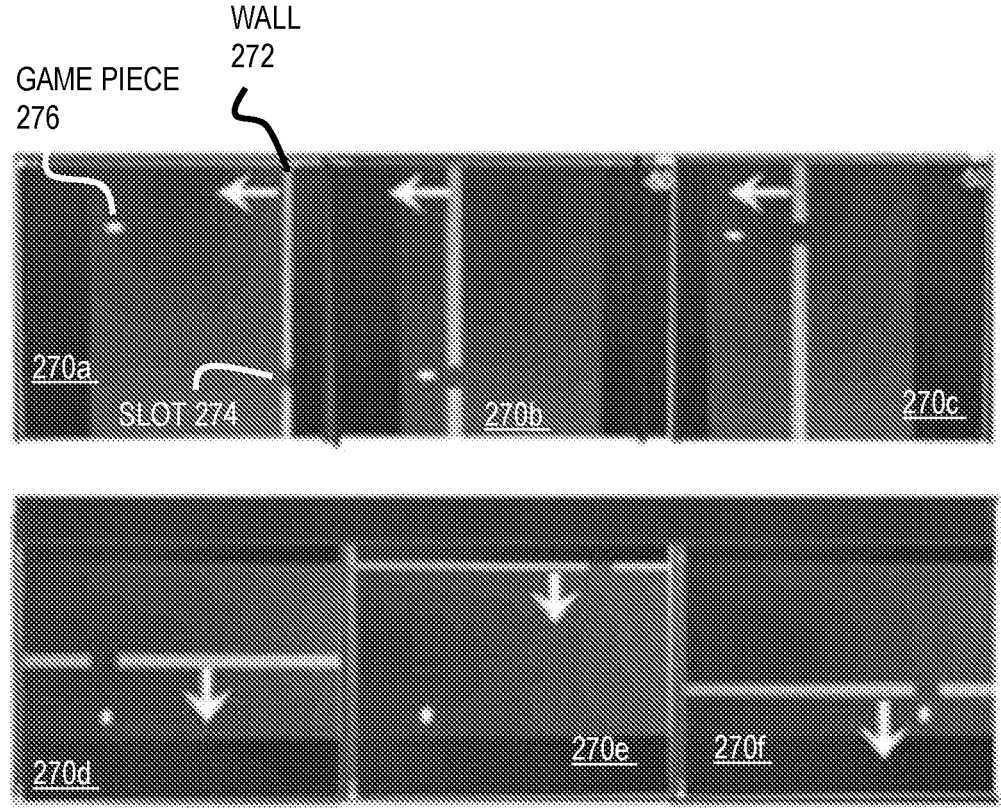

In FIG. 2F, six frames 270a, 270b, 270c, 270d, 270e and 270f of a race car video game presentation are depicted. Each frame includes a wall 272 with a small opening representing the tolerance slot 274. The object of the game is to drive a game piece 276 through the tolerance slot. The distance from the game piece 276 to the wall 272 is the remaining time in the current cycle or session and shrinks with time as indicated by the arrow attached to the wall 272 in each frame. The game piece 276 is moved parallel to the wall by relative motion of left and right handles. For example, the game piece 276 is not aligned with the slot 274 in frame 270a, but due to concerted bilateral effort by the subject is aligned with the slot by the time the wall approaches in frame 270b. After each slot is successfully navigated another wall with another opening is confronted and the game piece is aligned again by concerted bilateral effort as shown in frame 270c. In another configuration with vertically moving walls, frame 270d shows a game piece 276 aligned with the slot in the approaching wall 272, not aligned in frame 270e with the next approaching wall, and eventually again aligned with that next wall in the third frame 270f due to concerted bilateral effort by the subject.

Figure 2G:

In FIG. 2G, a GUI 280 is presented to improve inter-limb symmetry. GUI 280 includes one vertical track 282 configured as a bar graph. On this track is a single filled bar 286, which increases height with greater symmetry (a ratio of paretic to nonparetic, P/NP, excursion). A ratio of 100% indicates the P arm is keeping up with the NP arm. In the illustrated embodiment, the subject performance is at about a 35% ratio of P/NP. A target line 284 (set at 60% of maximum bar height recently achieved by the subject, which is at 30% if the previous maximum performance were 50%) represents the target trajectory and will move up or down depending on user performance every 10 complete extension-flexion cycles. A result greater than or equal to 60% of previous maximum ratio results in attainment/exceeding the line (or not) indexing "success" (or failure), the algorithm will move the line up (or down) by ±20% of its current value to make the task more difficult (or easy). This will consistently update goals based on user performance A counter will display cumulative score (10 points per "success") in score area 288. The settings can be manually overridden compared to default settings (e.g., initial target line location). Additionally, other GUI areas display key metrics for 30-sec time intervals re-computed every 50 cycles to be used by a PT to explain performance to the patient. Such metrics are exportable as a Report Card to be printed or transmitted to the patient or PT or both, e.g., via email. Other active areas, collectively called active areas 289, are depicted for selecting or inputting information, such as setting up the training session with initial parameter values in area 289a, starting the session using active area 289b, or applying a penalty or not in active areas 289c and 289d, respectively. Other areas 290 are customizable inputs. For example, 290a refers to the number of consecutive, complete movements for which the slot control strategy will be generated and set up. Similarly, 290b refers to the initial level of the goal bar. A higher value would be used, for example, for subjects with mild deficits (thereby giving them the appropriate challenge to begin with for initial motivation) and a lower value would be used for subjects with moderate to severe deficits (thereby avoiding initial frustration). Finally, 290c refers to a value for the maximum angle of the elbow of the nonparetic (NP) arm. in area 290c. This video game and scoring mechanisms provide not only feedback but reward and motivation to the subject.

Returning to FIG. 2A, following step 209, some of steps 211 through step 227 are performed in embodiments that include at least one impedance drive 134. In step 211, it is determined whether the force applied by the subject to the handles and detected at actuator 136 is increasing while the current handle position is within the tolerance slot for the target trajectory. If so, control passes to step 213 to have the motor be backdriven by the subject supplied force. In some embodiments this backdriving includes some tactile feedback to the subject in the form or viscous cushioning. In some embodiments, low stiction, as is the case with linear backdrivable actuators, provide little or no perception when the subject backdrives the hardware (e.g., when the subject's hand movements are within the slot). This allows the subject to not have to learn the intrinsic robot dynamics, which may be confounding for neurologically disabled populations, both from a tactile (proprioceptive) and/or cognitive standpoint(s). An example slot control strategy is simple: "push" or "pull" active assist (through programmable, virtual stiffness and damping) if outside the slot, and no assist if inside the slow. Control then passes to step 231, described below, to determine if the cycle is complete.

If it is determined in step 211 that the handle is not within the tolerance slot, or that the handle is in the tolerance slot but there is no force applied by the subject, then control passes to step 221. In step 221, it is determined if the handle is outside and behind the tolerance slot. If so, then in step 223 the motor and actuator are engaged to assist the subject by accelerating the handle and to record the assist or evaluate the work done by the motor or both. Any method may be used to record this motor operation as an excursion, such as by incrementing a motor count by one, or measuring the work done by the motor, such as the power drawn by the motor, or counting the revolutions of the motor. This recorded motor operation contributes to an objective metric and or a single score in some embodiments. For example, using a novel metric to quantify step-by-step human versus motor ("robot") contributions during assisted walking, it was shown that a robust ankle motor learning profile for reduced robot reliance was achieved concomitant with human autonomy for volitional swing clearance, collectively contributing to reduced reliance on assistive devices (85%) and increased daily free-living ambulatory activity (>20%), even six weeks after training ceases in adults with chronic stroke disability. Such a "co-robotic" metric is included in some embodiments. The co-robotic metric is applicable for any human-robot collaborative applications as long as a slot control strategy is employed. Basically, the metric counts the time spent inside the slot as a percent of total time for a complete (flexion or extension) movement. The rationale is that since the slot control will only assist the subject to reach the edges of the slot (if the subject's hand movements are outside the slot), the only way the subject can be inside the slot is through their own volitional effort. Hence, for most nondisabled individuals the co-robotic metric (also called Human Autonomy Index, or HAI) will be "high" (ideally 100%) while for impaired individuals the HAI will be "low" and will increase as recovery progresses. Control then passes to step 231, described below, to determine whether the current cycle is complete.

If it is determined in step 221 that the handle is not outside and behind the tolerance slot, then control passes to step 225. In step 225, it is determined if the handle is outside and ahead of the tolerance slot. If not, then control passes to step 231, described below, to determine whether the current cycle is complete. If so, then in step 227 the motor and actuator are engaged to assist the subject by decelerating the handle and to record the assist and work done by the motor. Any method may be used to record this motor operation as an excursion, such as by incrementing a motor count by one, or measuring the work done by the motor, such as the power drawn by the motor, or counting the revolutions of the motor or otherwise updating a "co-robotic" metric. This recorded motor operation contributes to an objective metric and or a single-valued score in some embodiments. Thus, by virtue of steps 223 and 227, the method includes operating a drive mechanically connected to the handle to reduce deviations of the measured time series outside the tolerance slot bracketing the trajectory; and, determining the objective metric involves determining the objective metric based at least in part on operating the drive. Control then passes to step 231, described below, to determine whether the current cycle is complete.

FIG. 2C is a plot that illustrates example forces applied by an impedance drive in response to the simulated arm movements depicted in FIG. 2B, according to an embodiment. The horizontal axis indicates elapsed time in units of time samples, as in FIG. 2B. The vertical axis indicates force applied by the impedance drive 134 to assist the simulated subject to return to within the tolerance slot. Times of zero force or viscous cushioning backdriven force are indicated by the x symbols. The triangles indicate times when the handle is outside the tolerance slot and a force is applied. Positive force accelerates the handle that is behind the tolerance slot; and negative force decelerates the handle that is ahead of the tolerance slot. The effect is to minimize the size of excursion that would otherwise occur, and thus speed recovery; but, the failure of the subject to perform unassisted is recorded so the occurrence impacts the objective metric anyway.

Returning to FIG. 2A, in step 231, it is determined whether the cycle is complete. This occurs, for example, when the handle 132 returns to its starting point closest to, or farthest from, the subject. This can also occur when the handle 132 reaches a minimum or maximum distance from the subject and reverses direction, whether or not that minimum or maximum is the same position as the start a previous cycle. If the cycle is not complete, then control passes back to step 207 and following described above to sense record and display based on the next sensor 131 detected position of the handle 132.

If it is determined in step 231 that the cycle is complete, then control passes to step 233. In step 233, the cycle stats are recorded, e.g., in fields 184 through 198 of cycle record 180. In some embodiments, step 233 also accumulates scores or other objective metric for the last several cycles, such as the single score at least since the target trajectory was last updated in step 203.

In step 235, it is determined if there are sufficient numbers of new cycles (e.g., in a number range from 10 to 100 cycles) to warrant an update to one or more target trajectories. If not, control passes back to step 207 and following for the next cycle. However, if there are sufficient number of new cycles, such as 10 cycles or 20 cycles or 50 cycles or 100 cycles, then control passes to step 203 to update a target trajectory based on the performance over these multiple new cycles. In some embodiments, no update is done until all the cycles in one session are completed. Thus, in some embodiments, the method includes modifying the target trajectory based at least in part on the objective metric. In some embodiments this is done by modifying, based at least in part on the objective metric, at least one of the specified range or the specified duration for the target trajectory.

For example, in step 203, if the score or objective metric is consistently poor, as determined from the accumulated metric over several cycles, then the range for the target trajectory is advantageously reduced or the period is advantageously increased or the tolerance is advantageously increased, or some combination, for the next cycle or number of cycles or the next session. In some embodiments, the change in any parameter's value is a percentage change based on one or more objective metrics or the single score. Conversely, if the score or objective metric is consistently good or close to maximum, as determined from the accumulated metric over several cycles, then the range for the target trajectory is advantageously increased or the period is advantageously decreased or the tolerance is advantageously decreased, or some combination, for the next cycle or number of cycles or next session. In some embodiments the change in any parameter values is a percentage change for the difference between the current target trajectory and the subject goal target trajectory stored in field 168 for the subject. In some embodiments, the percentage is based on one or more objective metrics or the single-valued score. The update is recorded in one or more fields of data structure 152. For example, in some embodiments, the updated range or period or tolerance is recorded in fields 182 or 183 for the next cycle, or fields 172 and 173 for the remainder of the session, or the field 166 for the next session for this subject.

If it is determined in step 205 that the session is complete, then in step 239 the final score for the session and any visual game reward is presented on the display 154 in video or auditory form or both. In some embodiments, step 239 includes sending a message to the caregiver at a terminal associated with that caregiver, the final score or any changes to the current target trajectory for the subject, or some combination. As a result, in some embodiments, the caregiver will prescribe further treatment for the subject. The process then ends.

An advantage of various embodiments is greater patient throughput, because PTs can initially determine the patient impairment-specific robotic settings (such as curve type, cycle range and cycle period) then let the robot "guide" the training. Since adaptive robotics makes semi-automated training possible, a single PT can provide therapy for multiple patients at the same time; compared to the 1:1 PT to patient conventional training setup. Another advantage of various embodiments is improved outcomes, by focusing on task specific training with adaptive robotic algorithms. This allows a neoplastic response allowing for neural recovery and improved reaching functions beyond usual care. Another advantage of various embodiments is providing objective robotic measures, enabling PTs to systematically guide therapy and quantitatively document patient improvements. Currently, functional recovery can only be measured either in expensive biomechanics labs or by therapists using instruments and testing protocols with limited and subjective output, such as goniometers. In contrast, various embodiments provide quantitative measures of function at the point-of-care. By adding objective measures to current clinical outcomes, clinics have adequate data to justify insurance extensions and treat patients beyond the usual cap. Another advantage of various embodiments is giving clinics that do regularly treat stroke the tools needed to effectively address neurologically impaired function in former patients and creating a new tool for clinics that do not regularly treat neurologically impaired patients a simple cost-effective method to draw on a new patient population. Also, by documenting the use of rehabilitation robotics, such facilities can obtain Commission on Accreditation of Rehabilitation Facilities (CARF International) credit for exemplar stroke care. Patients, providers, and payers recognize CARF accreditation as a demonstration of internationally accepted superior standards.

2. Example Embodiments

Figure 3:
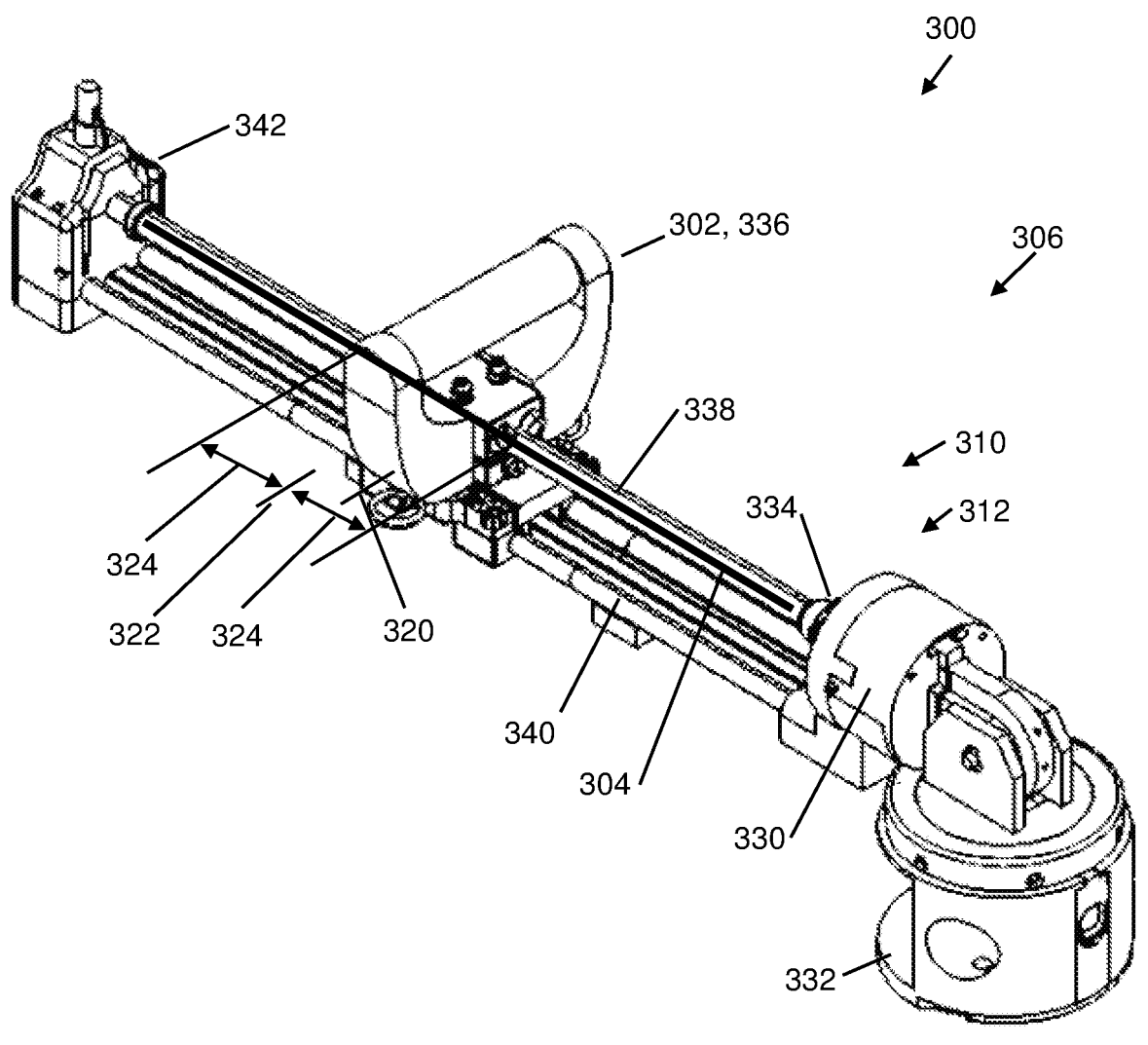
FIG. 3 is a perspective view of an example embodiment of a therapeutic device of the automated bilateral arm training system.
Figure 4:
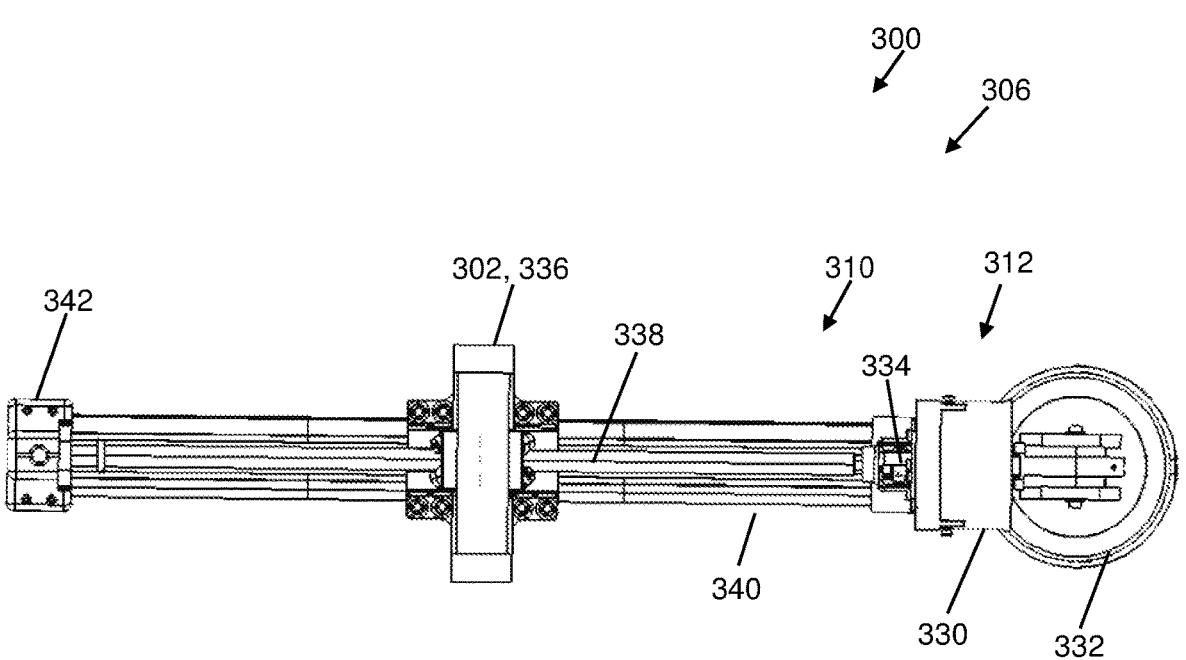
FIG. 4 is a top view of the therapeutic device of FIG. 3.
Figure 5:
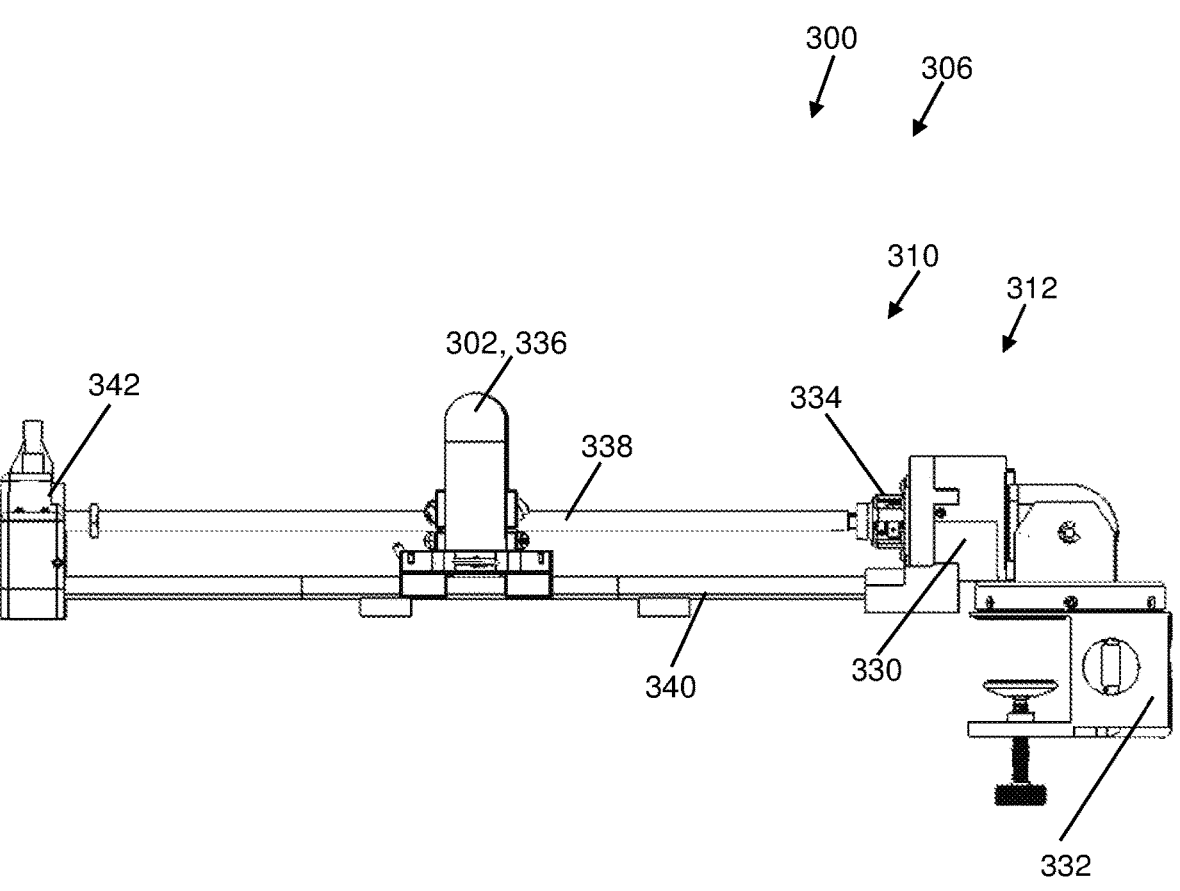
FIG. 5 is a side view of the therapeutic device of FIG. 3.

FIG. 3 to FIG. 5 show an example embodiment of a therapeutic device 300 of the bilateral arm training system 100. The bilateral arm training system 100 may include one or two therapeutic devices 300 that are arranged as shown in FIG. 1A. The therapeutic device 300 includes a handle 302 configured to move along a path 304; and an impedance-controlled assembly 306, also known as the handle drive assembly 130.

The impedance-controlled assembly 306 includes a sensor assembly 310 configured to track a position of the handle 302 along the path 304; and a handle drive assembly 312 secured to the handle 302. The impedance-controlled assembly 306 is configured to apply a position-correcting force to the handle 302 when an actual position 320 of the handle 302 deviates from an expected position 322 of the handle 302 by a tolerance 324. The tolerance may be predetermined and/or adjustable. The position-correcting force is configured to change a speed of the handle 302 and move the handle 302 toward the expected position 322. The position-correction force is also configured to apply no force to the handle 302 so long as the actual position 320 of the handle 302 is within the tolerance 324. As shown in FIG. 3, the actual position 320 of the handle 302 is within the tolerance 324 of the expected position 322 at the appropriate time. Hence, no position-correcting force would be applied to the handle 302 at the time the system is arranged as illustrated. In an example embodiment, if the actual position 320 is ahead of the expected position, the impedance-controlled assembly 306 is configured to resist the subject's efforts and is optionally further configured to push the handle 302 back toward the expected position 322 with a position-correcting force. Likewise, if the actual position 320 is behind the expected position, the impedance-controlled assembly 306 is configured to overcome the subject's resistance and is optionally further configured to push the handle 302 forward toward the expected position 322 with a position-correcting force.

In an example embodiment, the impedance-controlled assembly 306 is configured to move the expected position 322 over time to form a target trajectory along the path. The subject would then move the handle 302 over time in an effort to keep the actual position 320 of the handle 302 as close as possible to the expected position 322. As above, if the actual position 320 is within the tolerance 324 of the expected position 322, the impedance-controlled assembly 306 will exert no position-correcting force. If the actual position 320 is ahead or behind the expected position 322, the impedance-controlled assembly 306 will resist the subject's efforts and may be further configured to push the handle 302 toward the expected position 322 via a position-correcting force.

In a therapeutic environment, the subject's ability to remain within the tolerance 324 should improve over time. The magnitude of the tolerance can be relatively large to start and can decrease as the subject's ability increases. The subject's ability to stay within the tolerance 324 can be tracked and the improvement quantified. As noted above, the actual position 320, the expected position 322, and the tolerance 324 can be visually represented on the display 154. Further, these can be incorporated into a video game where the object is for the subject viewing the display 154 to keep the visually represented actual position within the visually represented tolerance of the visually represented expected position.

In an example embodiment, the impedance-controlled assembly 306 is configured to be imperceptible, or barely-perceptible to the subject when the actual position 320 is within the tolerance 324. This involves allowing the subject to be able to backdrive the impedance-controlled assembly 306. In contrast to when the actual position 320 is outside of the tolerance 324 and the impedance-controlled assembly 306 exerts corrective force on the handle 302, when the actual position 320 is within the tolerance 324, it is expected that the subject is to be in control of the position of the handle 302. Were this not the case, when inside the tolerance 324, a subject would still receive assistance from the impedance-controlled assembly 306. This may slow therapeutic progress. When the impedance-controlled assembly 306 provides reduced or no assistance, the subject will be forced to exert the control on the handle 302 and this may accelerate therapeutic progress.

Optionally, instead of providing no force, in an example embodiment, the impedance-controlled assembly 306 is configured to apply viscous cushioning when the actual position 320 is within the tolerance 324. Viscous cushioning cushions motion of the handle 302 but does not change a direction of movement of the handle 302. A magnitude of the viscous cushioning may be adjustable.

Using an impedance control scheme makes it possible for the impedance-controlled assembly 306 to sense and attempt to conform to the subject's will when the handle 302 is within the tolerance 324. However, the amount of conformity, e.g. the amount of backdrivability, and associated reduction in assistance, can be increased by focusing on mechanical aspects of the impedance-controlled assembly 306 as is detailed below.

The therapeutic device 300 further includes a motor housing assembly 330, a shoulder assembly 332, a bearing support assembly 334, an actuated slide mount assembly 336 that includes the handle 302, a linkage such as an actuated shaft 338 (e.g. a lead screw) which actuates the actuated slide mount assembly 336, a guide path assembly 340, and a back cap assembly 342. The example embodiments of each of these assemblies are not meant to be limiting. In a broad sense, the therapeutic device can function as intended with a handle that can be moved along a path (whether or not the movement along the path is guided by a rail or the like), and a sensor system that can track a position of the handle. For robot assist, the device also includes an effector (not necessarily impedance controlled) that can effect movement of the handle as disclosed above. The embodiments below represent various reductions to practice deemed respectively appropriate to reach certain performance, economy, and adaptability levels. However, the embodiments are not necessarily required for the therapeutic device to perform at difference performance, economic, and adaptability levels, and hence are not limiting. For example, the impedance-controlled assembly could be a fully articulated robotic arm and the movement of the handle could be fully unconstrained. In such an embodiment, the path could be any path imaginable and could be straight, curved, and any combination of both. In such an embodiment, the sensor system could be a type that is able to locate the handle anywhere in a field, such as an optical sensor or the like. The reductions chosen below represent what is understood by the inventors to be an efficient blend of function, cost, and modularity that is most likely to result in therapeutic benefit to the greatest number of those in need.

Figure 6:
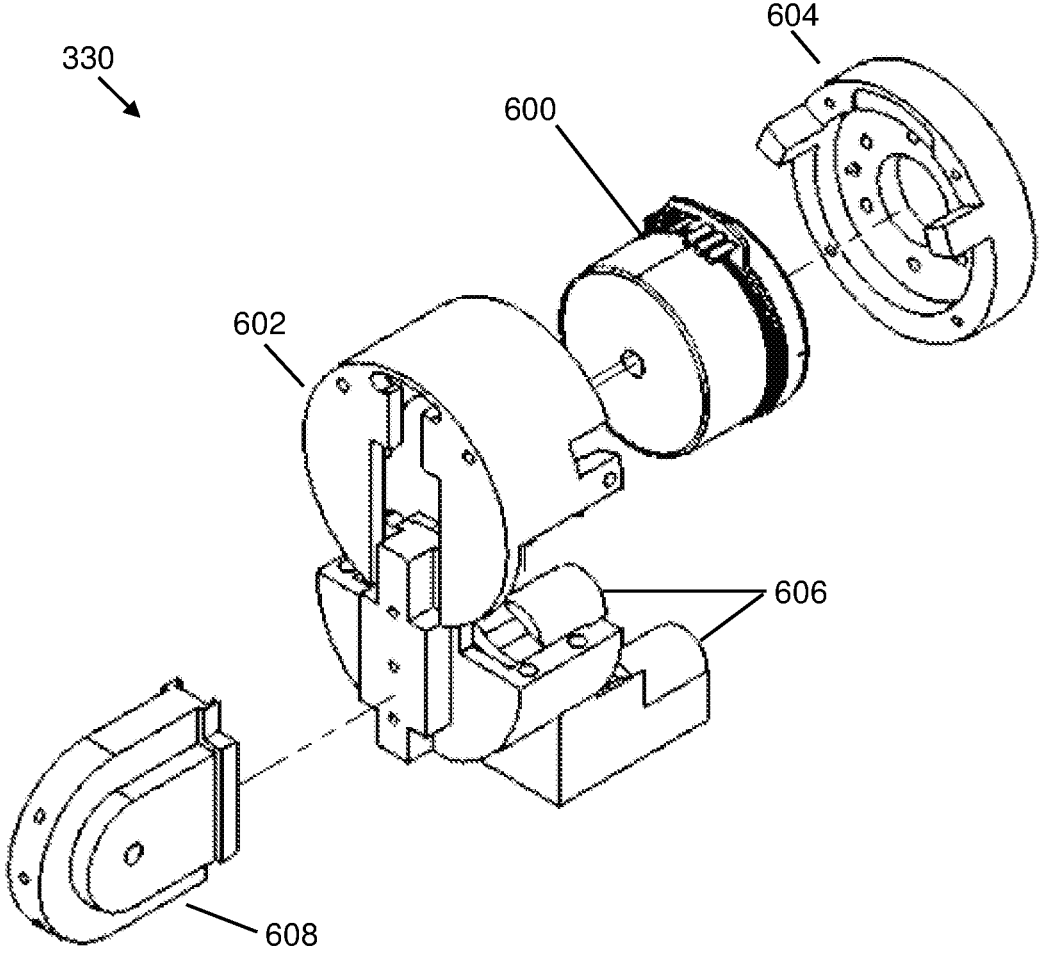
FIG. 6 is an exploded view of an example embodiment of a motor housing assembly of the therapeutic device of FIG. 3.
Figure 7:
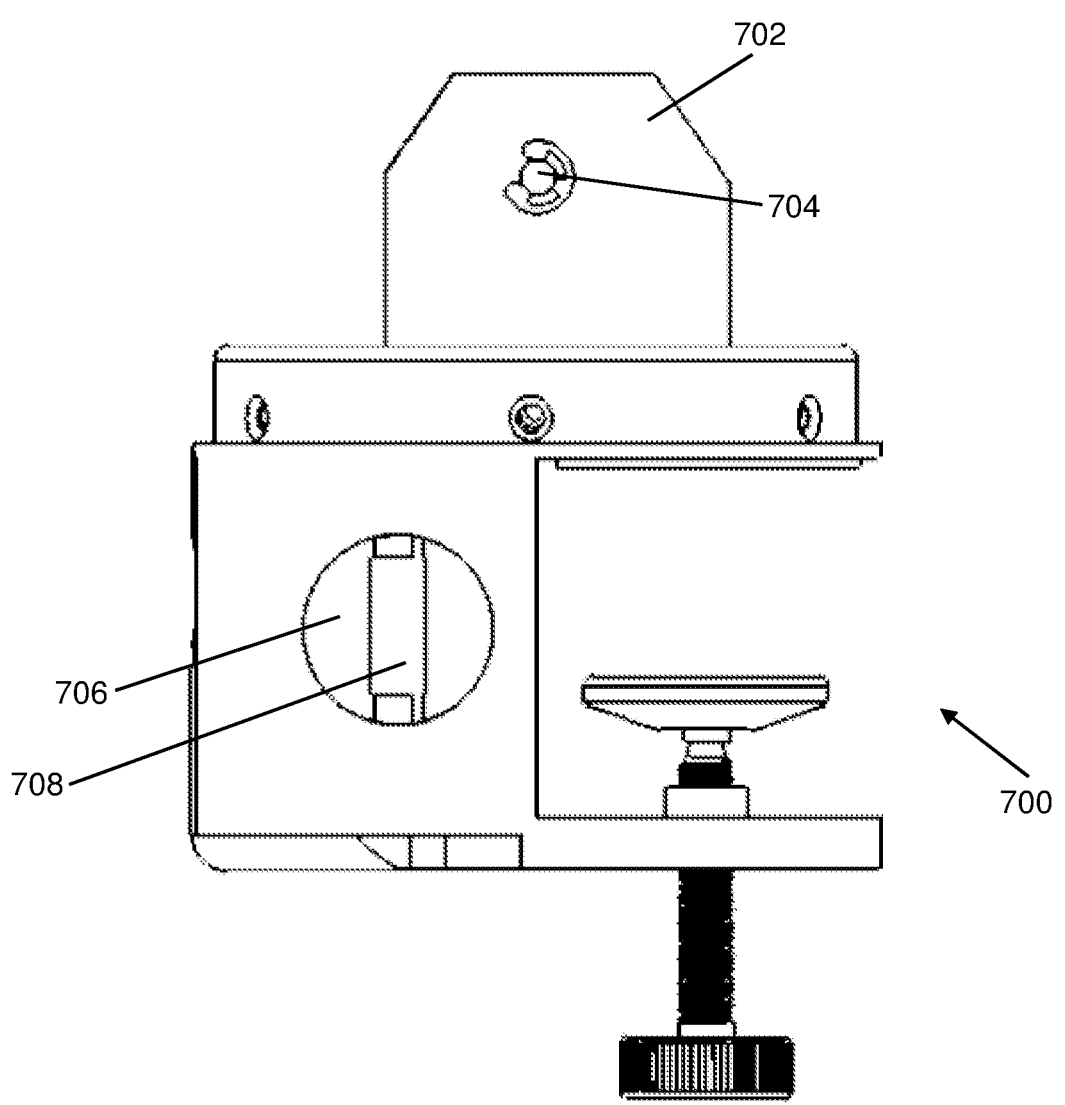
FIG. 7 is a side view of an example embodiment of a shoulder assembly of the therapeutic device of FIG. 3.
Figure 8:
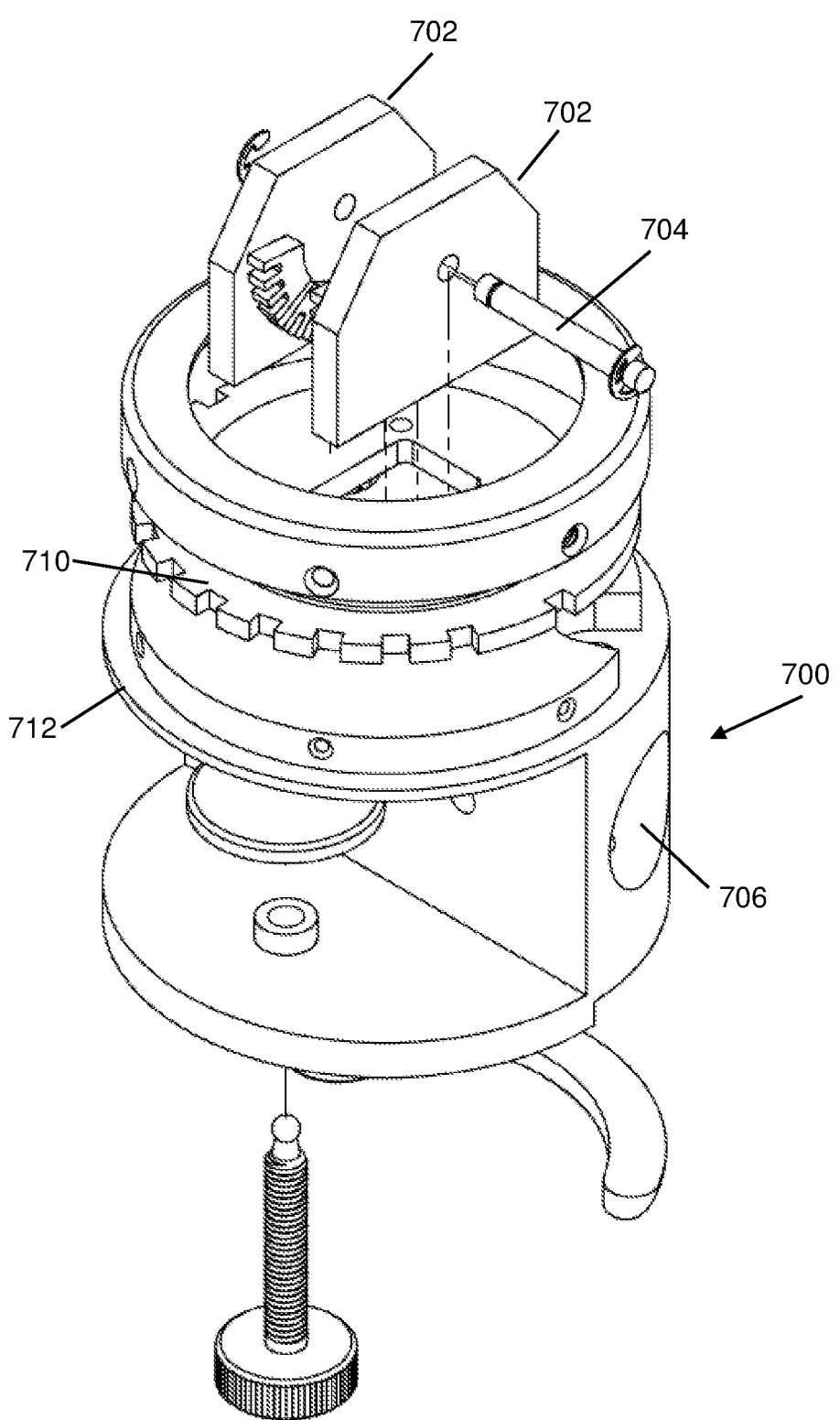
FIG. 8 is an exploded view of the shoulder assembly of FIG. 7

FIG. 6 is an exploded view of an example embodiment of the motor housing assembly 330 of the therapeutic device 300. The motor housing assembly 330 encapsulates and protects the motor 600 and houses the bearing support assembly 334. The motor 600 is disposed within a motor housing frame 602 with a removable motor housing cover 604 that allows access to the motor 600, and the bearing support subassembly 334. The motor housing subassembly 330 includes a motor housing guide rail constraint 606 that constrains a proximate end of the guide path assembly 340. Attached to the motor housing frame 602 is a motor housing base 608 that pivotally secures the motor housing assembly 330 to the shoulder assembly 332. In an example embodiment, the motor 600 is a position-controlled (e.g., DC) motor. A suitable motor 600 is rated for at least 8 Newton-meters of continuous stall torque. An example suitable motor 600 is an EC 60 flat Ø60 mm, brushless motor by Maxon Group of Taunton MA FIG. 7 and FIG. 8 show an example embodiment of the shoulder assembly 332 of the therapeutic device 300. The shoulder assembly 332 includes a clamp assembly 700 configured to attach the shoulder assembly 332 to a table or surface (not shown), and vertical trunnions 702 that support a pin 704. The trunnions 702 and the pin 704 receive the motor housing base 608 and enable the motor housing base 608 to pivot around the pin 704. The motor housing base 608, the trunnions 702, and the pin 704 constitute a pivot joint that enables the motor housing assembly 330 to be manually rotated relative to the reference surface such as a tabletop. The shoulder assembly 332 further includes a thru-hole 706 that receives a horizontal bar (not shown) that can be used to connect the shoulder assemblies 332 of two different therapeutic devices 300 and the chest support 114. The horizontal bar may be secured within the thru-hole 706 via a quick-release pin 708 that makes assembly and disassembly quick and easy. Trunnions 702 and their attached gear plate 710 can be rotated/positioned with respect to the shoulder base 712 and then assembled onto the shoulder base 712. Once assembled, this rotation is locked by the pin (not visible) on the back side of the shoulder base 712 meshing with the gear plate 710.

Figure 9:
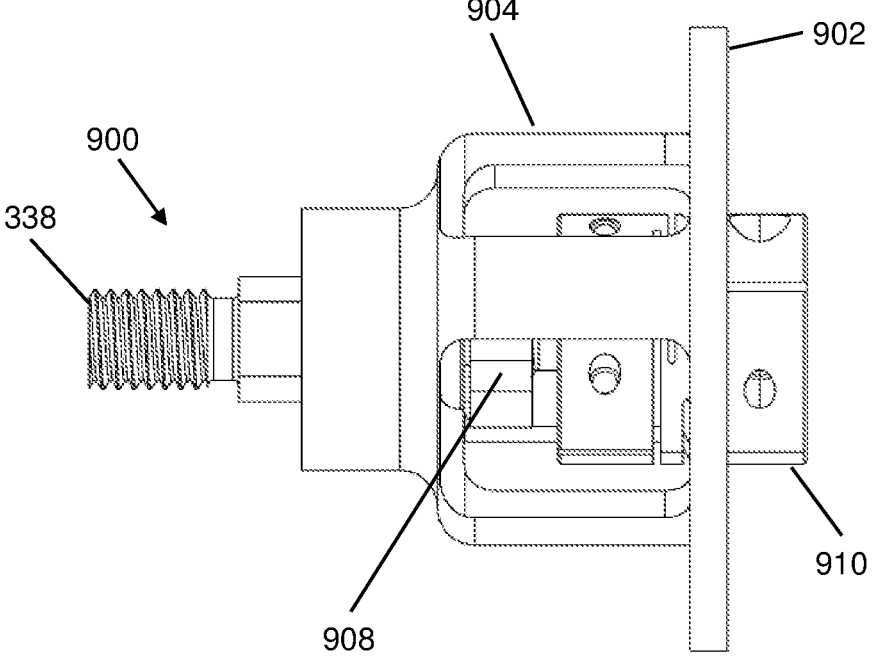
FIG. 9 is a perspective view of an example embodiment of a bearing support assembly of the therapeutic device of FIG. 3.
Figure 10:
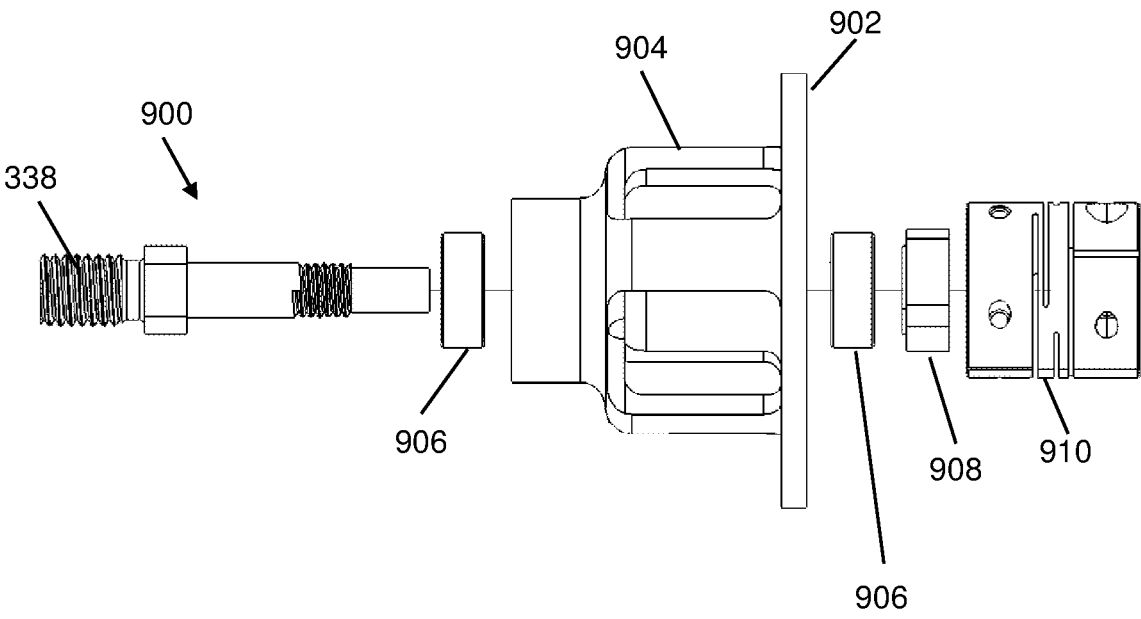
FIG. 10 is an exploded view of the bearing support assembly of FIG. 9.

FIG. 9 and FIG. 10 show an example embodiment of the bearing support assembly 334 of the therapeutic device 300. The bearing support assembly 334 couples a motor shaft (not shown) to a proximate end 900 of the actuated shaft 338, allowing the motor 600 to rotate the actuated shaft 338. A flange 902 of a bearing support frame 904 secures the bearing support assembly 334 to the motor housing frame 602 and/or the motor housing cover 604. Two thrust bearings 906 and a lock nut 908 secure the proximate end 900 of the actuated shaft 338 to the bearing support frame 904, while a collar 910 secures the proximate end 900 of the actuated shaft 338 to the motor shaft. This ensures the actuated shaft 338 freely rotates with minimal friction.

Figure 12:
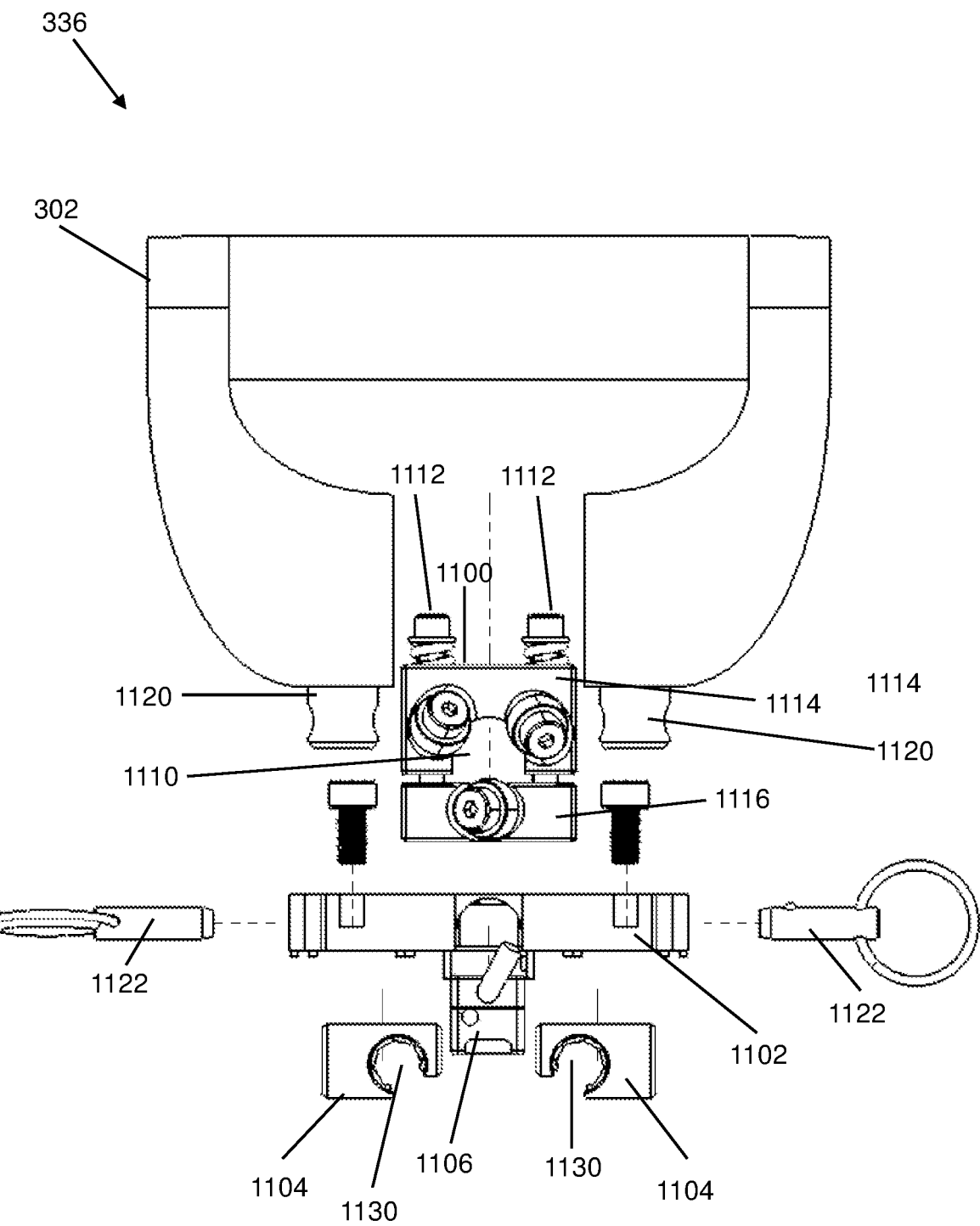
FIG. 12 is an exploded view of the actuated slide mount assembly of FIG. 11.

FIG. 11 and FIG. 12 show an example embodiment of the actuated slide mount assembly 336 of the therapeutic device 300. The actuated slide mount assembly 336 includes the handle 302, a linear actuator 1100, a slide mount frame 1102, pillow blocks 1104 (e.g. four), and a sensor 1106. The linear actuator 1100 includes an actuator thru-hole 1110 configured to receive the actuated shaft 338 therein. The linear actuator 1100 is configured to convert rotary motion of the actuated shaft 338 into linear motion of the actuated slide mount assembly 336.

In an example embodiment, the linear actuator 1100 is a low stiction (<1 Newton-meter full torque range) linear actuator. An example suitable linear actuator 1100 is a Roh'Lix® linear actuator manufactured by Zero-Max of Plymouth, MN The Roh'Lix® linear actuator includes six rolling element ball bearings that contact the actuated shaft 338 at an angle. Thrust adjustment spring screw assemblies 1112 permit adjustment of an amount of spring force between two block halves 1114, 1116. The spring force determines an amount of thrust the Roh'Lix® linear actuator can accommodate before the Roh'Lix® linear actuator begins to slip on the actuated shaft 338. This creates an overload protection for the therapeutic device 300.

The slide mount frame 1102 includes handle receptacles (not visible) that receive handle protrusions 1120 and pins 1122 that readily releasably secure the handle protrusions 1120, and likewise the handle 302, in the slide mount frame 1102. The handle 302 may be configured to support the subject's hand in pure pronation, to support the hand 45° supinated from fully-prone, or to support the hand or to support the hand 90° supinated from fully-prone. The therapeutic device 300 may therefore include three or more handles 302, each having a different configuration. Alternately, the handle may be configured to rotate about one or more axis to accommodate a range of motion of the subject's hand during use. The pillow blocks 1104 allow the actuated slide mount assembly 336 to slide along rails of the guide path assembly 340 with minimal friction by receiving the rails within pillow block through holes 1130.

The sensor 1106 is part of the sensor assembly 310 and is configured to provide information about a position of the actuated slide mount assembly 336 relative to the path 304. The sensor 1106 is mounted to the slide mount frame 1102 and may be a relative or absolute encoder. In an example embodiment, the sensor 1106 is an absolute encoder configured to cooperate with an encoder track associated with the path 304.

As noted above, the amount of conformity, e.g. the amount of backdrivability, and associated reduction in assistance, can be increased by focusing on mechanical aspects of the impedance-controlled assembly 306 e.g. to reduce stiction. One mechanical aspect is an inertia of the actuated slide mount assembly 336. Namely, the lower the inertia, the more responsive the actuated slide mount assembly 336 is to lighter inputs by the subject's hand. In an example embodiment, a suitable inertia results when the actuated slide mount assembly 336 has a mass of 0.6 to 1.5 kilograms. A suitable friction for the actuated slide mount assembly 336 is 0.5 to 1.1 Newtons. In an example embodiment, the impedance-controlled assembly 306 generates from zero to 45 Newtons of force on the actuated slide mount assembly 336. Acceptable impedance is from zero to 2 Newtons/millimeter.

Another mechanical aspect can be in the mechanical connection within and between the impedance-controlled assembly 306 and the actuated slide mount assembly 336. For example, the mechanical connection between the impedance-controlled assembly 306 and the actuated slide mount assembly 336 could be traditional gears with intermeshing teeth. However, these assemblies have inherent backlash, greater friction, and resist being backdriven. The subject then encounters and overcomes these characteristics in order to backdrive the device. Hence, in those circumstances, the device is working against the subject specifically when the device is intended to be invisible to the subject. The Roh'Lix® linear actuator significantly reduces backlash, friction, and resistance to backdriving, and this enables the therapeutic device 300 to respond much more readily to the subtle inputs of a subject rehabilitating a paretic arm.

Figure 13:
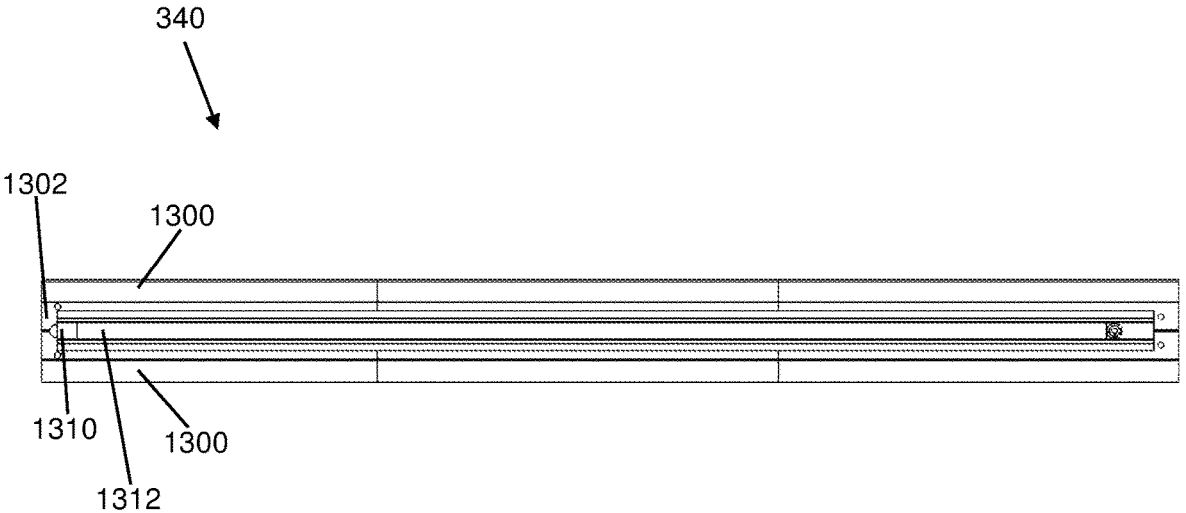
FIG. 13 is a top view of an example embodiment of a guide path assembly of the therapeutic device of FIG. 3.
Figure 14:
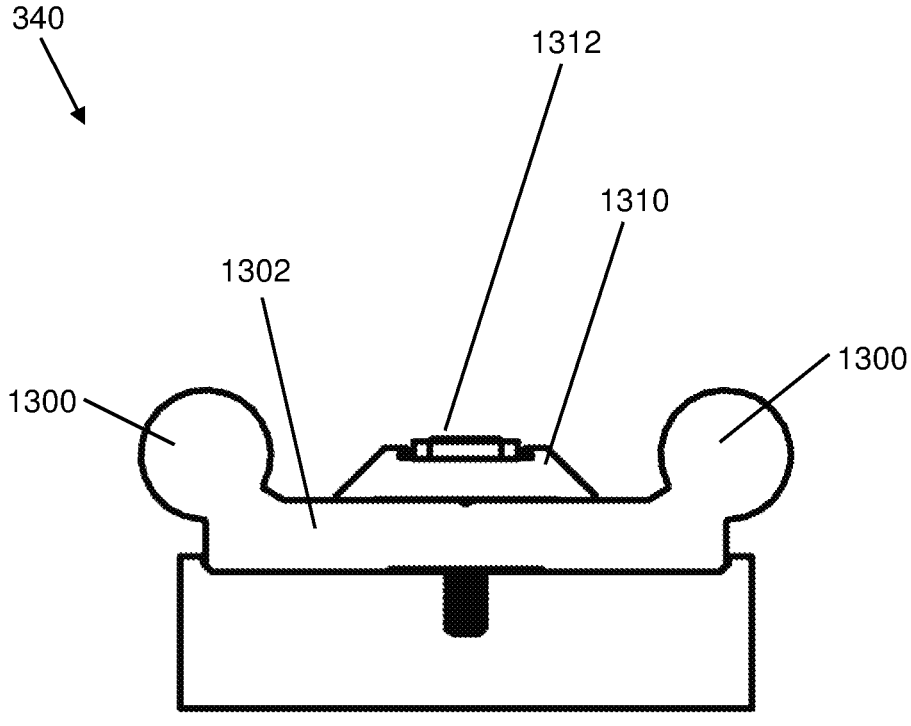
FIG. 14 is an end view of the guide path assembly of FIG. 13.

FIG. 13 and FIG. 14 show an example embodiment of the guide path assembly 340 of the therapeutic device 300. The guide path assembly 340 supports the actuated slide mount assembly 336 and allows it to move with minimal friction. The guide path assembly 340 includes two guide rails 1300 connected to a guide rail body 1302 and configured to fit into the pillow block through holes 1130 of the pillow blocks 1104. The actuated slide mount assembly 336 moves along the actuated shaft 338, and the actuated slide mount assembly 336 also moves along the guide rails 1300. In the illustrated example embodiment, the actuated shaft 338 and the guide rails 1300 rails are parallel to each other. Hence, the actuated shaft 338 determines the path 304 as do the guide rails 1300. However, this is not mandatory. For example, in embodiments where the linkage is not an actuated shaft 338, but is instead unconstrained, like a fully articulated robot arm, the guide rails along 1300 may determine the path 304. Likewise, if no guide rails are present, the actuated shaft 338 alone may determine the path 304. In example embodiments in which the linkage does not define the path and there are no constraining guide rails, the path may be virtual and shown on the video monitor. In such an embodiment, the subject would be required to properly position the handle 302 within tolerances in all three dimensions relative to the expected positions. Affixed to the guide rail body 1302 is an encoder track housing 1310, which in turn contains an encoder track 1312 that provides a reference for the sensor 1106. In an example embodiment, the encoder track 1312 is a magnetic encoder track. Since the encoder track 1312 is associated with the guide rails 1300, and since the guide rails 1300 are associated with the path 304, the encoder track 1312 is naturally also associated with the path 304.

Figure 15:
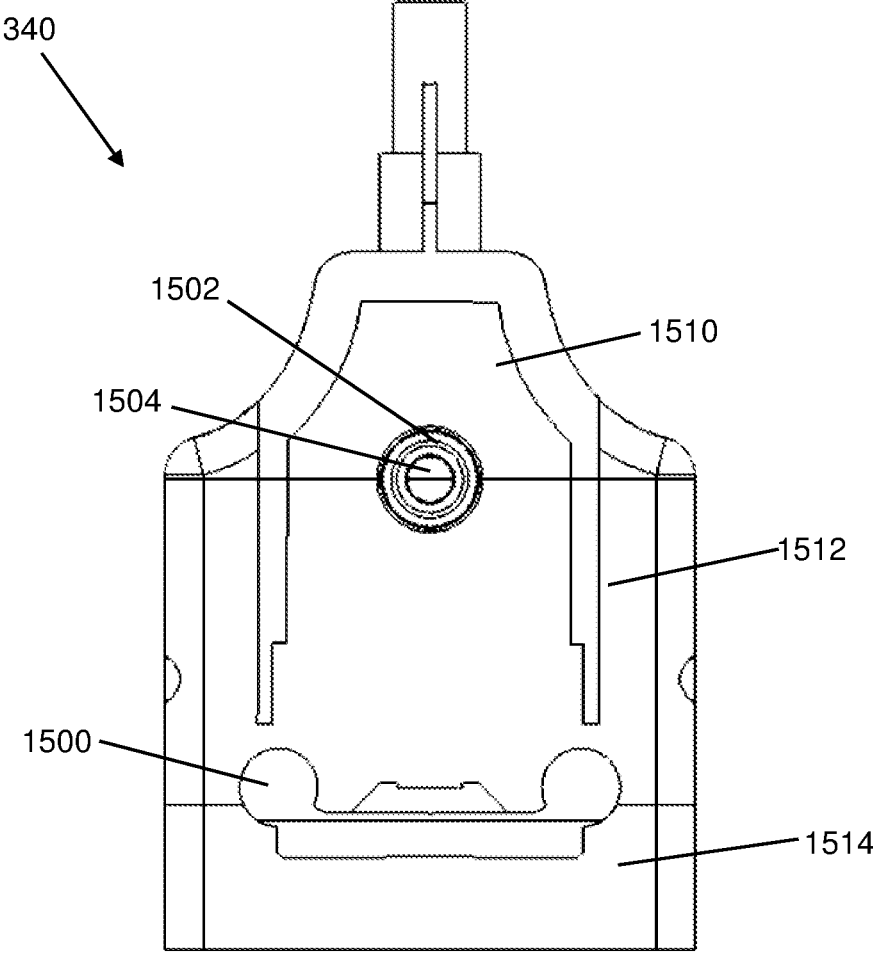
FIG. 15 is a front view of an example embodiment of a back cap assembly of the therapeutic device of FIG. 3.
Figure 16:
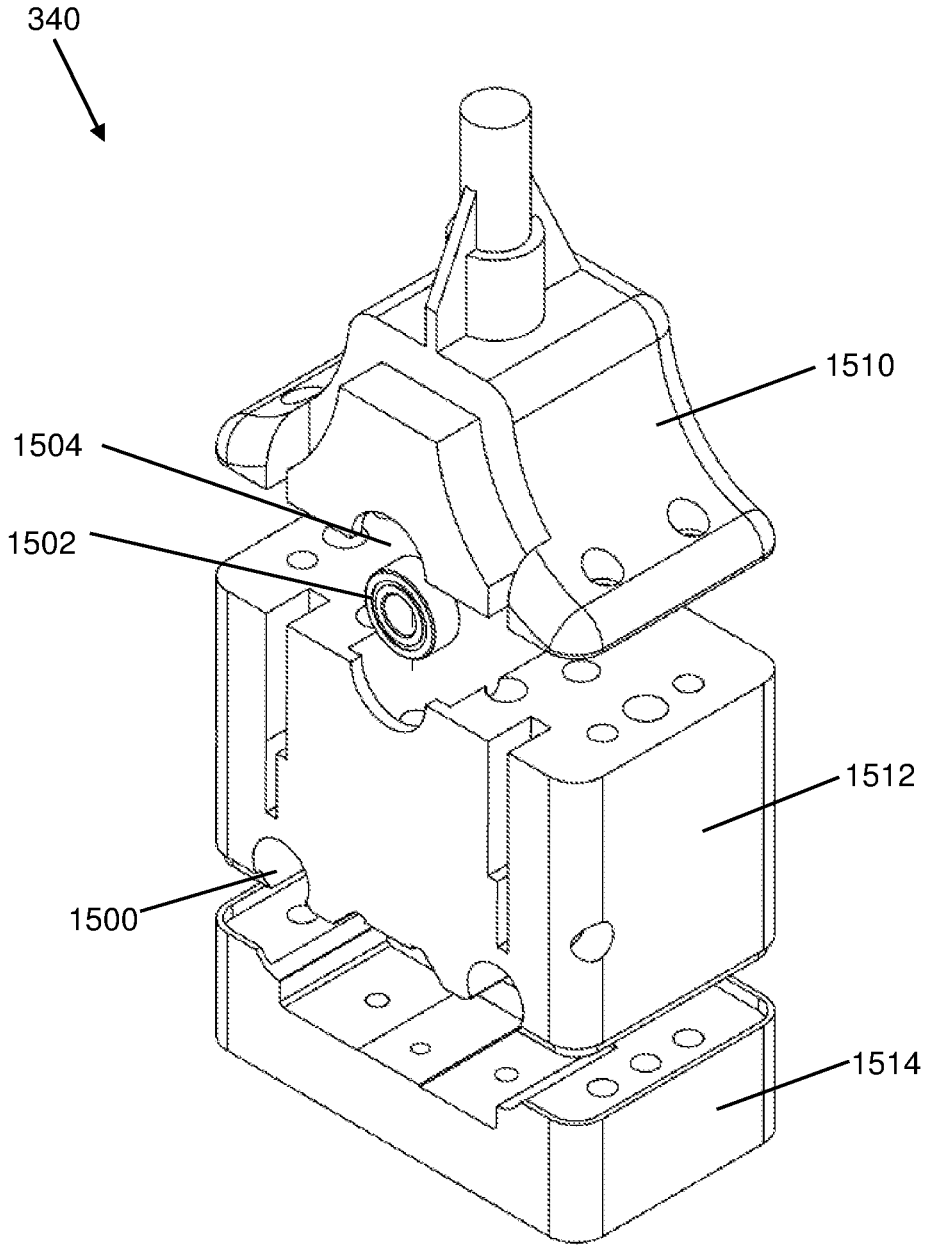
FIG. 16 is an exploded view of the back cap assembly of FIG. 15.

FIG. 15 and FIG. 16 show an example embodiment of the back cap assembly 342 of the therapeutic device 300. The back cap assembly 342 houses a distal end of the guide rails 1300 in a back cap guide rail constraint 1500. Similarly, the back cap assembly 342 houses a distal end of the actuated shaft 338 in a back cap actuated shaft bearing 1502 which is disposed in a back cap actuated shaft bearing receptacle 1504. The back cap assembly 342 includes plural blocks 1510, 1512, 1514 which can be readily assembled together onto the distal end of the guide rails 1300 and the back cap actuated shaft bearing 1502 and likewise readily disassembled. In the example embodiment shown, the guide rails 1300 are fully constrained. In contrast, the back cap actuated shaft bearing 1502 is a free-floating bearing, giving the actuated shaft 338 both rotational and linear freedom in the axial direction while constraining all others.

FIG. 17 is a perspective view of an alternate example embodiment of the handle 1700 having a rotating connection 1702 to the slide mount frame (not shown). The rotating connection 1702 permits the handle 1700 to rotate about a vertical axis 1704 to follow the natural motion of the subject's hand during use.

FIG. 18 is a perspective view of another alternate example embodiment of the handle 1800 also having the rotating connection 1802 to the slide mount frame (not shown). The rotating connection 1802 permits the handle 1800 to rotate about the vertical axis 1804 to follow the natural motion of the subject's hand during use.

Thus, the illustrated embodiment is configured to provide an impedance-controlled, modular arm trainer interfaced with a "smart" visual task, further including the benefits of actuation-control, instrumentation, and visual feedback for use as a lowest-cost in-class training device for stroke rehabilitation.

3. Computational Hardware Overview

Figure 19:
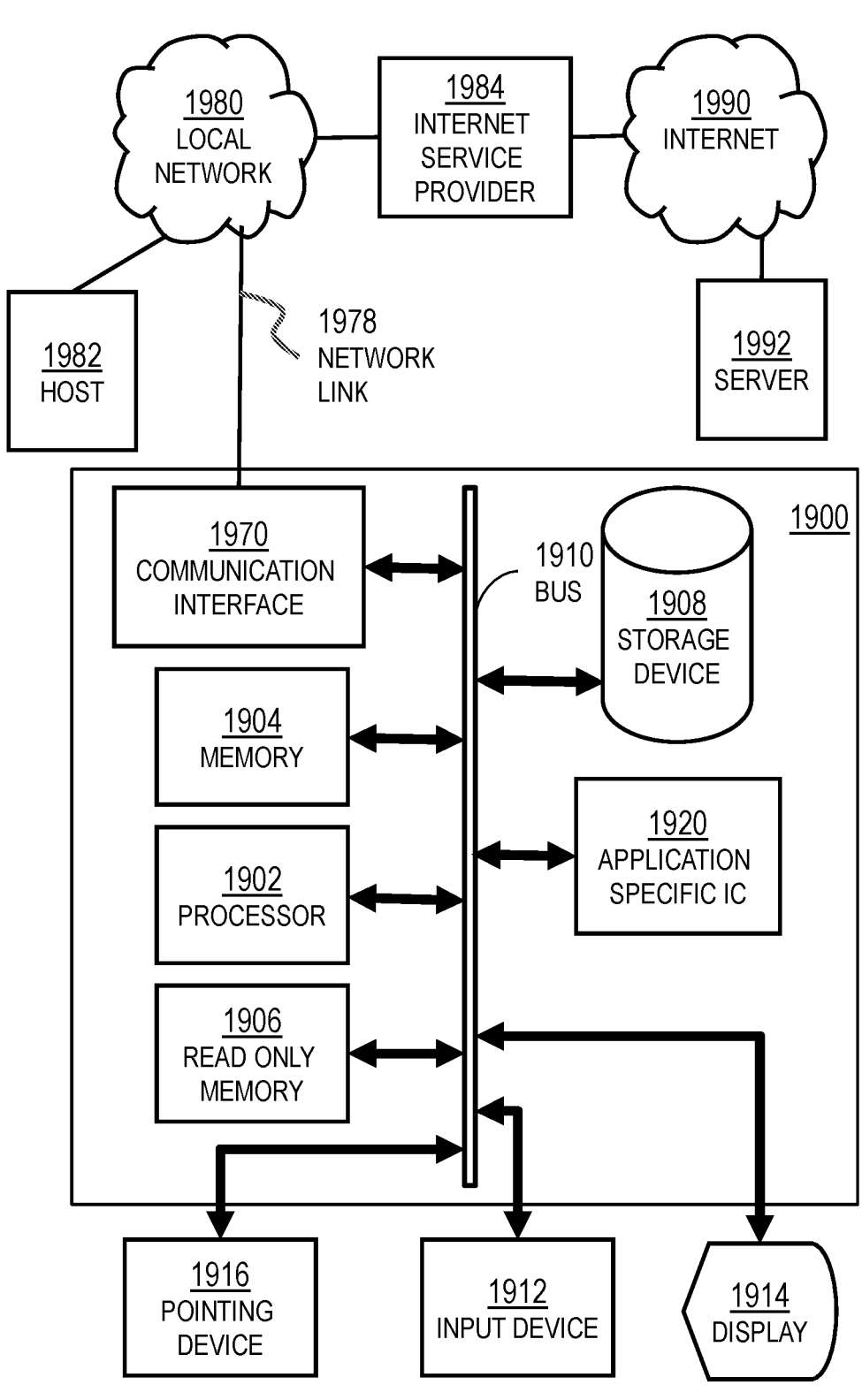
FIG. 19 is a block diagram that illustrates a computer system upon which an embodiment of the invention may be implemented.

FIG. 19 is a block diagram that illustrates a computer system 1900 upon which an embodiment of the invention may be implemented. Computer system 1900 includes a communication mechanism such as a bus 1910 for passing information between other internal and external components of the computer system 1900. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1900, or a portion thereof, constitutes a means for performing one or more steps of one or more methods described herein.

A sequence of binary digits constitutes digital data that is used to represent a number or code for a character. A bus 1910 includes many parallel conductors of information so that information is transferred quickly among devices coupled to the bus 1910. One or more processors 1902 for processing information are coupled with the bus 1910. A processor 1902 performs a set of operations on information. The set of operations include bringing information in from the bus 1910 and placing information on the bus 1910. The set of operations also typically include comparing two or more units of information, shifting positions of units of information, and combining two or more units of information, such as by addition or multiplication. A sequence of operations to be executed by the processor 1902 constitutes computer instructions.

Computer system 1900 also includes a memory 1904 coupled to bus 1910. The memory 1904, such as a random access memory (RAM) or other dynamic storage device, stores information including computer instructions. Dynamic memory allows information stored therein to be changed by the computer system 1900. RAM allows a unit of information stored at a location called a memory address to be stored and retrieved independently of information at neighboring addresses. The memory 1904 is also used by the processor 1902 to store temporary values during execution of computer instructions. The computer system 1900 also includes a read only memory (ROM) 1906 or other static storage device coupled to the bus 1910 for storing static information, including instructions, that is not changed by the computer system 1900. Also coupled to bus 1910 is a non-volatile (persistent) storage device 1908, such as a magnetic disk or optical disk, for storing information, including instructions, that persists even when the computer system 1900 is turned off or otherwise loses power.

Information, including instructions, is provided to the bus 1910 for use by the processor from an external input device 1912, such as a keyboard containing alphanumeric keys operated by a human user, or a sensor. A sensor detects conditions in its vicinity and transforms those detections into signals compatible with the signals used to represent information in computer system 1900. Other external devices coupled to bus 1910, used primarily for interacting with humans, include a display device 1914, such as a cathode ray tube (CRT) or a liquid crystal display (LCD), for presenting images, and a pointing device 1916, such as a mouse or a trackball or cursor direction keys, for controlling a position of a small cursor image presented on the display 1914 and issuing commands associated with graphical elements presented on the display 1914.

In the illustrated embodiment, special purpose hardware, such as an application specific integrated circuit (IC) 1920, is coupled to bus 1910. The special purpose hardware is configured to perform operations not performed by processor 1902 quickly enough for special purposes. Examples of application specific ICs include graphics accelerator cards for generating images for display 1914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1900 also includes one or more instances of a communications interface 1970 coupled to bus 1910. Communication interface 1970 provides a two-way communication coupling to a variety of external devices that operate with their own processors, such as printers, scanners and external disks. In general the coupling is with a network link 1978 that is connected to a local network 1980 to which a variety of external devices with their own processors are connected. For example, communication interface 1970 may be a parallel port or a serial port or a universal serial bus (USB) port on a personal computer. In some embodiments, communications interface 1970 is an integrated services digital network (ISDN) card or a digital subscriber line (DSL) card or a telephone modem that provides an information communication connection to a corresponding type of telephone line. In some embodiments, a communication interface 1970 is a cable modem that converts signals on bus 1910 into signals for a communication connection over a coaxial cable or into optical signals for a communication connection over a fiber optic cable. As another example, communications interface 1970 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1970 sends and receives electrical, acoustic or electromagnetic signals, including infrared and optical signals, that carry information streams, such as digital data.

The term computer-readable medium is used herein to refer to any medium that participates in providing information to processor 1902, including instructions for execution. Such a medium may take many forms, including, but not limited to, non-volatile media, volatile media and transmission media. Non-volatile media include, for example, optical or magnetic disks, such as storage device 1908. Volatile media include, for example, dynamic memory 1904. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1902, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1902, except for carrier waves and other signals.

Logic encoded in one or more tangible media includes one or both of processor instructions on a computer-readable storage media and special purpose hardware, such as ASIC 1920.

Network link 1978 typically provides information communication through one or more networks to other devices that use or process the information. For example, network link 1978 may provide a connection through local network 1980 to a host computer 1982 or to equipment 1984 operated by an Internet Service Provider (ISP). ISP equipment 1984 in turn provides data communication services through the public, world-wide packet-switching communication network of networks now commonly referred to as the Internet 1990. A computer called a server 1992 connected to the Internet provides a service in response to information received over the Internet. For example, server 1992 provides information representing video data for presentation at display 1914.

The invention is related to the use of computer system 1900 for implementing the techniques described herein. According to one embodiment of the invention, those techniques are performed by computer system 1900 in response to processor 1902 executing one or more sequences of one or more instructions contained in memory 1904. Such instructions, also called software and program code, may be read into memory 1904 from another computer-readable medium such as storage device 1908. Execution of the sequences of instructions contained in memory 1904 causes processor 1902 to perform the method steps described herein. In alternative embodiments, hardware, such as application specific integrated circuit 1920, may be used in place of or in combination with software to implement the invention. Thus, embodiments of the invention are not limited to any specific combination of hardware and software.

The signals transmitted over network link 1978 and other networks through communications interface 1970, carry information to and from computer system 1900. Computer system 1900 can send and receive information, including program code, through the networks 1980, 1990 among others, through network link 1978 and communications interface 1970. In an example using the Internet 1990, a server 1992 transmits program code for a particular application, requested by a message sent from computer 1900, through Internet 1990, ISP equipment 1984, local network 1980 and communications interface 1970. The received code may be executed by processor 1902 as it is received, or may be stored in storage device 1908 or other non-volatile storage for later execution, or both. In this manner, computer system 1900 may obtain application program code in the form of a signal on a carrier wave.

Various forms of computer readable media may be involved in carrying one or more sequence of instructions or data or both to processor 1902 for execution. For example, instructions and data may initially be carried on a magnetic disk of a remote computer such as host 1982. The remote computer loads the instructions and data into its dynamic memory and sends the instructions and data over a telephone line using a modem. A modem local to the computer system 1900 receives the instructions and data on a telephone line and uses an infra-red transmitter to convert the instructions and data to a signal on an infra-red a carrier wave serving as the network link 1978. An infrared detector serving as communications interface 1970 receives the instructions and data carried in the infrared signal and places information representing the instructions and data onto bus 1910. Bus 1910 carries the information to memory 1904 from which processor 1902 retrieves and executes the instructions using some of the data sent with the instructions. The instructions and data received in memory 1904 may optionally be stored on storage device 1908, either before or after execution by the processor 1902.

Figure 20:
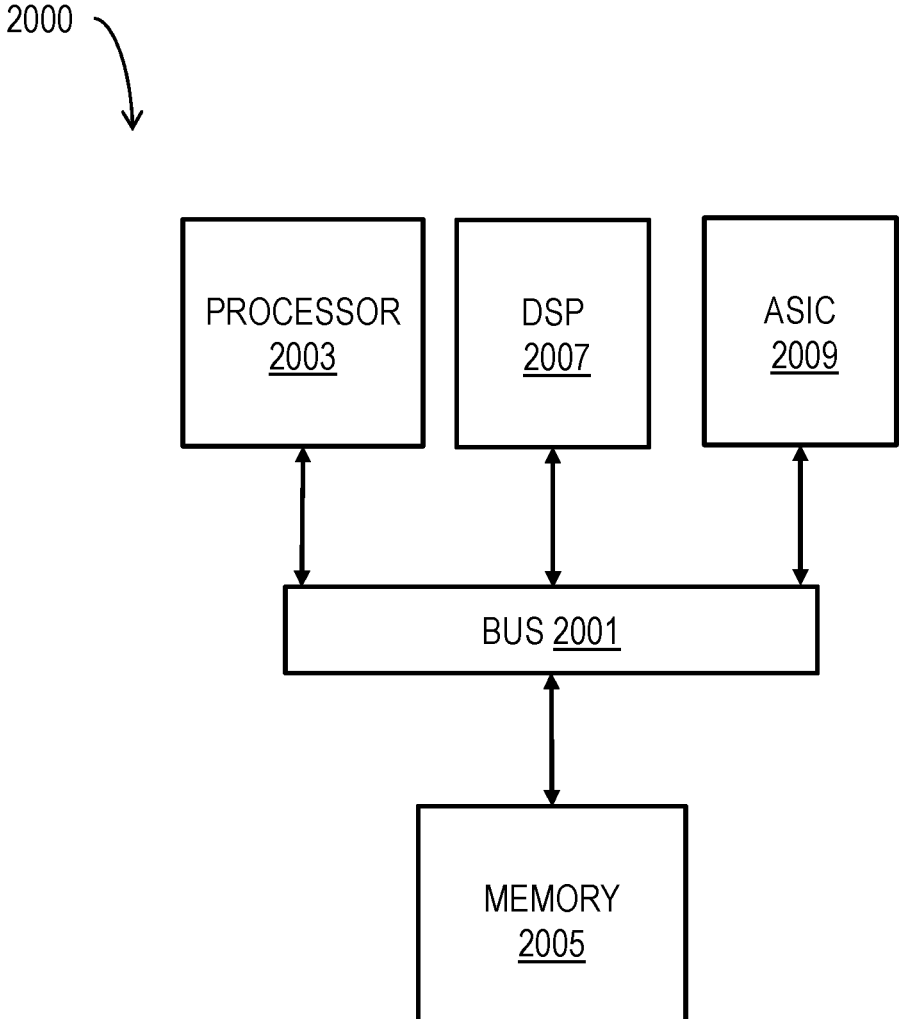
FIG. 20 is a block diagram that illustrates a example chip set upon which an embodiment of the invention may be implemented.

FIG. 20 is a block diagram that illustrates an example chip set 2000 upon which an embodiment of the invention may be implemented. Chip set 2000 is programmed to perform one or more steps of a method described herein and includes, for instance, the processor and memory components described with respect to FIG. 19 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2000, or a portion thereof, constitutes a means for performing one or more steps of a method described herein.

In one embodiment, the chip set 2000 includes a communication mechanism such as a bus 2001 for passing information among the components of the chip set 2000. A processor 2003 has connectivity to the bus 2001 to execute instructions and process information stored in, for example, a memory 2005. The processor 2003 may include one or more processing cores with each core configured to perform independently. A multi-core processor enables multiprocessing within a single physical package. Examples of a multi-core processor include two, four, eight, or greater numbers of processing cores. Alternatively or in addition, the processor 2003 may include one or more microprocessors configured in tandem via the bus 2001 to enable independent execution of instructions, pipelining, and multithreading. The processor 2003 may also be accompanied with one or more specialized components to perform certain processing functions and tasks such as one or more digital signal processors (DSP) 2007, or one or more application-specific integrated circuits (ASIC) 2009. A DSP 2007 typically is configured to process real-world signals (e.g., sound) in real time independently of the processor 2003. Similarly, an ASIC 2009 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2003 and accompanying components have connectivity to the memory 2005 via the bus 2001. The memory 2005 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2005 also stores the data associated with or generated by the execution of one or more steps of the methods described herein.

Figure 21:
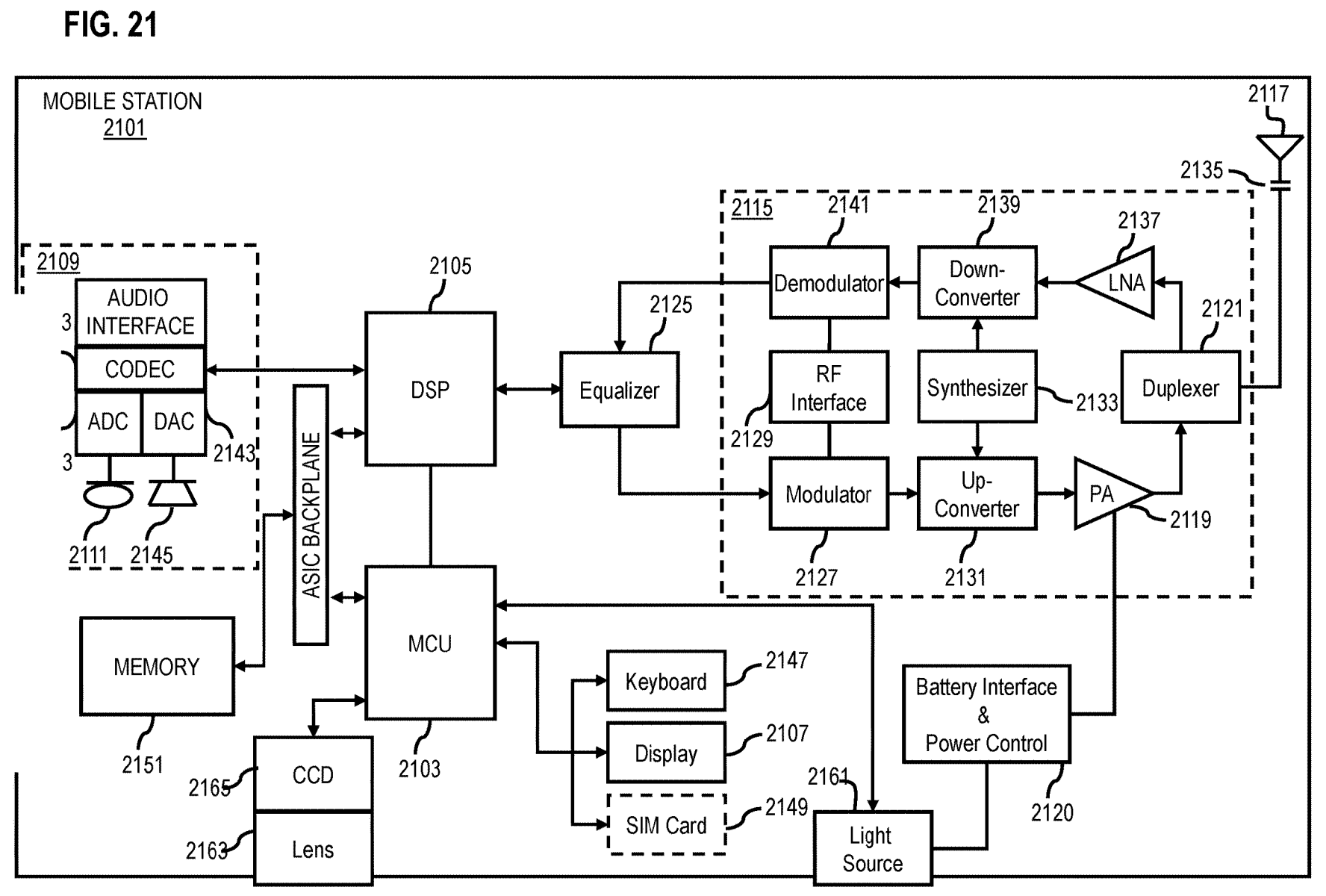

FIG. 21 is a diagram of example components of a mobile terminal 2100 (e.g., cell phone handset) for communications, which is capable of operating in the system of FIG. 1A, according to one embodiment. In some embodiments, mobile terminal 2101, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 2103, a Digital Signal Processor (DSP) 2105, and a receiver/transmitter unit including a microphone gain control unit and a speaker gain control unit. A main display unit 2107 provides a display to the user in support of various applications and mobile terminal functions that perform or support the steps as described herein. The display 2107 includes display circuitry configured to display at least a portion of a user interface of the mobile terminal (e.g., mobile telephone). Additionally, the display 2107 and display circuitry are configured to facilitate user control of at least some functions of the mobile terminal. An audio function circuitry 2109 includes a microphone 2111 and microphone amplifier that amplifies the speech signal output from the microphone 2111. The amplified speech signal output from the microphone 2111 is fed to a coder/decoder (CODEC) 2113.

A radio section 2115 amplifies power and converts frequency in order to communicate with a base station, which is included in a mobile communication system, via antenna 2117. The power amplifier (PA) 2119 and the transmitter/modulation circuitry are operationally responsive to the MCU 2103, with an output from the PA 2119 coupled to the duplexer 2121 or circulator or antenna switch, as known in the art. The PA 2119 also couples to a battery interface and power control unit 2120.

In use, a user of mobile terminal 2101 speaks into the microphone 2111 and his or her voice along with any detected background noise is converted into an analog voltage. The analog voltage is then converted into a digital signal through the Analog to Digital Converter (ADC) 2123. The control unit 2103 routes the digital signal into the DSP 2105 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 2125 for compensation of any frequency-dependent impairments that occur during transmission though the air such as phase and amplitude distortion. After equalizing the bit stream, the modulator 2127 combines the signal with a RF signal generated in the RF interface 2129. The modulator 2127 generates a sine wave by way of frequency or phase modulation. In order to prepare the signal for transmission, an up-converter 2131 combines the sine wave output from the modulator 2127 with another sine wave generated by a synthesizer 2133 to achieve the desired frequency of transmission. The signal is then sent through a PA 2119 to increase the signal to an appropriate power level. In practical systems, the PA 2119 acts as a variable gain amplifier whose gain is controlled by the DSP 2105 from information received from a network base station. The signal is then filtered within the duplexer 2121 and optionally sent to an antenna coupler 2135 to match impedances to provide maximum power transfer. Finally, the signal is transmitted via antenna 2117 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 2101 are received via antenna 2117 and immediately amplified by a low noise amplifier (LNA) 2137. A down-converter 2139 lowers the carrier frequency while the demodulator 2141 strips away the RF leaving only a digital bit stream. The signal then goes through the equalizer 2125 and is processed by the DSP 2105. A Digital to Analog Converter (DAC) 2143 converts the signal and the resulting output is transmitted to the user through the speaker 2145, all under control of a Main Control Unit (MCU) 2103 which can be implemented as a Central Processing Unit (CPU) (not shown).

The MCU 2103 receives various signals including input signals from the keyboard 2147. The keyboard 2147 and/or the MCU 2103 in combination with other user input components (e.g., the microphone 2111) comprise a user interface circuitry for managing user input. The MCU 2103 runs a user interface software to facilitate user control of at least some functions of the mobile terminal 2101 as described herein. The MCU 2103 also delivers a display command and a switch command to the display 2107 and to the speech output switching controller, respectively. Further, the MCU 2103 exchanges information with the DSP 2105 and can access an optionally incorporated SIM card 2149 and a memory 2151. In addition, the MCU 2103 executes various control functions required of the terminal. The DSP 2105 may, depending upon the implementation, perform any of a variety of conventional digital processing functions on the voice signals. Additionally, DSP 2105 determines the background noise level of the local environment from the signals detected by microphone 2111 and sets the gain of microphone 2111 to a level selected to compensate for the natural tendency of the user of the mobile terminal 2101.

The CODEC 2113 includes the ADC 2123 and DAC 2143. The memory 2151 stores various data including call incoming tone data and is capable of storing other data including music data received via, e.g., the global Internet. The software module could reside in RAM memory, flash memory, registers, or any other form of writable storage medium known in the art. The memory device 2151 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 2149 carries, for instance, important information, such as the cellular phone number, the carrier supplying service, subscription details, and security information. The SIM card 2149 serves primarily to identify the mobile terminal 2101 on a radio network. The card 2149 also contains a memory for storing a personal telephone number registry, text messages, and user specific mobile terminal settings.

In some embodiments, the mobile terminal 2101 includes a digital camera comprising an array of optical detectors, such as charge coupled device (CCD) array 2165. The output of the array is image data that is transferred to the MCU for further processing or storage in the memory 2151 or both. In the illustrated embodiment, the light impinges on the optical array through a lens 2163, such as a pin-hole lens or a material lens made of an optical grade glass or plastic material. In the illustrated embodiment, the mobile terminal 2101 includes a light source 2161, such as a LED to illuminate a subject for capture by the optical array, e.g., CCD 2165. The light source is powered by the battery interface and power control module 2120 and controlled by the MCU 2103 based on instructions stored or loaded into the MCU 2103.

4. Alternatives, Deviations and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus, a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" for a positive only parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

What is claimed is:

1. A therapeutic device, comprising:
a handle that is configured to move along a path in response to a manual force applied to the handle and that is secured to a guide rail, wherein the guide rail defines the path;
a sensor assembly configured to provide a measured time series comprising a plurality of handle location measurements relative to the path at a corresponding plurality of measured time instances;
a display configured to present an image based on the measured time series; and
a pivot joint secured to an end of the guide rail, configured to be secured to a reference surface, and configured to pivot the guide rail relative to the reference surface, wherein the guide rail is cantilevered from the pivot joint.

2. The therapeutic device of claim 1, further comprising:
a handle drive assembly secured to the handle and configured to apply position-correcting force to the handle when the measured time series indicates an actual position of the handle which deviates from target trajectory for the handle by a predetermined tolerance, and is configured to apply no position-correcting force to the handle so long as the actual position of the handle is within the predetermined tolerance.

3. The therapeutic device of claim 2, wherein the handle drive assembly is configured to be backdriven by the handle only when the actual position of the handle is within the predetermined tolerance.

4. The therapeutic device of claim 2, wherein the handle drive assembly is configured not to apply viscous cushioning to the handle so long as the actual position of the handle is within the predetermined tolerance.

5. The therapeutic device of claim 1, wherein the sensor assembly is configured to track an absolute position of the handle along the path.

6. The therapeutic device of claim 1, wherein the sensor assembly comprises an absolute encoder configured to move along the path with the handle, and a linear encoder track that extends along the path and that provides a location reference for the absolute encoder.

7. The therapeutic device of claim 2, wherein the handle drive assembly comprises a position-controlled DC motor secured to the handle via a linkage.

8. The therapeutic device of claim 7, wherein the linkage comprises a lead screw secured to the DC motor and a linear actuator configured to convert rotation of the lead screw into translation of the handle.

9. The therapeutic device of claim 8, wherein the linear actuator comprises a Roh'Lix actuator secured to the linear actuator and to the handle.

10. The therapeutic device of claim 1, further comprising a handle frame secured to the guide rail, configured to receive the handle, and configured to move along the path with the handle in response to the manual force.

11. The therapeutic device of claim 1, further comprising a stop adjustably positionable along the guide rail and configured to define an end of the path.

12. The therapeutic device of claim 1, further comprising a chest support configured to abut a user's chest to hold the user in a proper position relative to the therapeutic device, wherein the manual force comprises a pull force, and wherein the chest support is configured to transfer at least a portion of the pull force to the user's chest.

13. The therapeutic device of claim 1, further comprising two handles, one for each hand of a user.

14. An automatic method for providing arm training, the method comprising:

receiving first data that indicates a target trajectory for movement along a path of a handle of a therapeutic device, wherein the handle is configured to be held at a distal end of an arm of a subject, is configured to move along the path in response to a manual force applied to the handle, and is secured to a guide rail, and wherein the guide rail defines the path, wherein the therapeutic device further comprises a pivot joint secured to an end of the guide rail, configured to be secured to a reference surface, and configured to pivot the guide rail relative to the reference surface, and wherein the guide rail is cantilevered from the pivot joint;

operating a sensor configured to provide a measured time series comprising a plurality of handle location measurements at a corresponding plurality of measured time instances;

determining an objective metric for the subject based at least in part on deviations of the measured time series from the target trajectory; and, presenting on a display an image based on the objective metric.

15. The method of claim 14, wherein:

the first data further indicates a second target trajectory for movement of a different second handle configured to be held at a distal end of a different second arm of the subject;

the sensor is further configured to provide a different second measured time series comprising a plurality of second handle location measurements at a second corresponding plurality of measured time instances; and said determining the objective metric further comprises determining the objective metric based at least in part on second deviations of the second measured time series from the second target trajectory.

16. The method of claim 15, wherein the first target trajectory and the second target trajectory are the same.

17. The method of claim 15, wherein the sensor comprises a first sensor configured to provide the measured time series and a different second sensor configured to provide the second measured time series.

18. The method of claim 14, wherein:

first data further indicates a tolerance slot bracketing the target trajectory; and said determining the objective metric further comprises determining the objective metric based at least in part on deviations of the measured time series from the tolerance slot bracketing the target trajectory.

19. The method of claim 18, further comprising operating a drive mechanically connected to the handle to reduce deviations of the measured time series outside the tolerance slot bracketing the trajectory.

20. The method of claim 19, wherein said determining the objective metric further comprises determining the objective metric based at least in part on said operating the drive.

21. The method of claim 14, further comprising modifying the target trajectory based at least in part on the objective metric.

22. The method of claim 14, wherein the target trajectory is a curve of minimum jerk for a path of specified range and a cycle of specified period.

23. The method of claim 22, further comprising modifying based at least in part on the objective metric at least one of the specified range or the specified period.

24. A non-transitory computer-readable medium carrying one or more sequences of instructions, wherein execution of the one or more sequences of instructions by one or more processors causes the one or more processors to perform the steps of:

receiving first data that indicates a target trajectory for movement along a path of a handle of a therapeutic device, wherein the handle is configured to be held at a distal end of an arm of a subject, is configured to move along the path in response to a manual force applied to the handle, and is secured to a guide rail, and wherein the guide rail defines the path, wherein the therapeutic device further comprises a pivot joint secured to an end of the guide rail, configured to be secured to a reference surface, and configured to pivot the guide rail relative to the reference surface, and wherein the guide rail is cantilevered from the pivot joint;

operating a sensor configured to provide a measured time series comprising a plurality of handle location measurements at a corresponding plurality of measured time instances;

determining an objective metric for the subject based at least in part on deviations of the measured time series from the target trajectory; and, presenting on a display an image based on the objective metric.

25. An apparatus comprising:

a display device;

at least one processor; and at least one memory including one or more sequences of instructions, the at least one memory and the one or more sequences of instructions configured to, with the at least one processor, cause the apparatus to perform at least the following:

receiving first data that indicates a target trajectory for movement along a path of a handle, wherein the handle is configured to be held at a distal end of an arm of a subject, is configured to move along the path in response to a manual force applied to the handle, and is secured to a guide rail, and wherein the guide rail defines the path;

operating a sensor configured to provide a measured time series comprising a plurality of handle location measurements relative to the path at a corresponding plurality of measured time instances;

determining an objective metric for the subject based at least in part on deviations of the measured time series from the target trajectory;

presenting on a display an image based on the objective metric;

wherein the apparatus comprises the handle, the arm, the guide rail, the sensor, and a pivot joint secured to an end of the guide rail, configured to be secured to a reference surface, and configured to pivot the guide rail relative to the reference surface, and wherein the guide rail is cantilevered from the pivot joint.

* * * * *